(12) United States Patent
Robins et al.

(10) Patent No.: US 7,737,253 B2
(45) Date of Patent: Jun. 15, 2010

(54) HUMAN CANCER STEM CELL CULTURE COMPOSITIONS COMPRISING ERBB2 VARIANTS AND METHODS OF USE THEREOF

(75) Inventors: Allan J. Robins, Athens, GA (US); Thomas C. Schulz, Athens, GA (US)

(73) Assignee: BresaGen, Inc., Athens, GA (US)

( * ) Notice: Subject to any disclaimer, the term of this patent is extended or adjusted under 35 U.S.C. 154(b) by 0 days.

(21) Appl. No.: 11/764,752

(22) Filed: Jun. 18, 2007

(65) Prior Publication Data

US 2008/0085557 A1 Apr. 10, 2008

Related U.S. Application Data

(60) Provisional application No. 60/805,039, filed on Jun. 16, 2006.

(51) Int. Cl.
*C07K 14/00* (2006.01)
*C12N 15/85* (2006.01)

(52) U.S. Cl. ........................... 530/350; 435/455
(58) Field of Classification Search ................. 530/350; 435/455
See application file for complete search history.

(56) References Cited

U.S. PATENT DOCUMENTS

| 5,811,098 | A | 9/1998 | Plowman et al. |
| 6,528,060 | B1 | 3/2003 | Nicolette |
| 6,632,979 | B2 | 10/2003 | Erickson et al. |
| 6,984,522 | B2 | 1/2006 | Clarke et al. |
| 7,060,279 | B2 | 6/2006 | Laus et al. |
| 2002/0001587 | A1* | 1/2002 | Erickson et al. .......... 424/178.1 |

OTHER PUBLICATIONS

Alignment data printed from the SCORE results for PCT/US07/71486, pp. 1-3.*
Akiyama et al., 1986, "The Product of the Human c-erbB-2 Gene: A 185-Kilodalton Glycoprotein with Tyrosine Kinase Activity," Science, 232:1644-46.
Anderson et al., 1993, "High-Density Genetic Map of the BRCA1 Region of Chromosome 17q12-q21," Genomics, 17:618-623.
Brimble et al., 2004, "Karyotypic Stability, Genotyping, Differentiation, Feeder-Free Maintenance, and Gene Expression Sampling in Three Human Embryonic Stem Cell Lines Derived Prior to Aug. 9, 2001," Stem Cells Dev., 13(6):585-97.
Brumlik et al., 2003, Poster, Faseb Summer Research Conference, "Growth Factor Receptor Tyrosine Kinases in Mitogenesis, Morphogenesis, & Tumorigenesis, Conference," Omni-Tucson, Tucson, AZ.
Castiglioni et al., 2006, "Role of Exon-16-Deleted HER2 in Breast Carcinomas," Endocr. Relat. Cancer, 13(1):221-32.
Coussens et al., 1985, "Tyrosine Kinase Receptor with Extensive Homology to EGF Receptor Shares Chro . . . ," Science, 230:1132-1139.
Cowan et al., 2004, "Derivation of Embryonic Stem-Cell Lines from Human Blastocysts," N. Engl. J. Med., 350 (13):1353-6.
De Placido et al., 1998, "c-erbB2 Expression Predicts Tamoxifen Efficacy in Breast Cancer Patients," Breast Cancer Res. Treat., 52:55-64.
Di Fiore et al., 1987, "erbB-2 is a Potent Oncogene when Overexpressed in NIH/3T3 Cells," Science, 237:178-182.
Doherty et al., 1999, "The HER-2 / neu Receptor Tyrosine Kinase Gene Encodes a Secreted Inhibitor," Proc. Nat. Acad. Sci., 96:10869-10874.
Draper et al., 2004, "Recurrent Gain of Chromosomes 17q and 12 in Cultured Human Embyronic Stem Cells," Nat. Biotechnol., 22(1):53-4.
Draper et al., 2004, "Culture and Characterization of Human Embryonic Stem Cells," Stem Cells Dev., 13(4):325-36.
Falls, 2003, "Neurogulins: Functions, Forms, and Signaling Strategies," Exp. Cell. Res., 284:14-30.
Fukushige et al., 1986, "Localization of a Novel v-erbB-Related Gene, c-erbB-2, on Human Chromosome 17 and its Amplification in a Gastric Cancer Cell Line," Mol. Cell. Biol., 6:955-958.
Jones et al., 1999, "Binding Specificities and Affinities of egf Domains for ErbB Receptors," FEBS Lett., 447:227-231.
Kaneko et al., 1987, "Human c-erbB-2 Remains on Chromosome 17 in Band q21 in the 15:17 Translocation Association with Acute Promyelocytic Leukemia," Jpn. J. Cancer Res., 78:16-19.
Kun et al., 2003, "Classifying the Estrogen Receptor Status of Breast Cancers by Expression Profiles Reveals a Poor Prognosis Subpopulation Exhibiting High Expression of the ERBB2 Receptor," Hum. Mol. Genet. 12:3245-3258.
Ludwig et al., 2006, "Derivation of Human Embryonic Stem Cells is Defined Conditions," Nature Biotechnol., 24 (2):185-87.
Maitra et al., 2005, "Genomic Alterations in Cultured Human Embryonic Stem Cells," Nat. Genet., 37(10):1099-103.

(Continued)

*Primary Examiner*—Thaian N Ton
*Assistant Examiner*—Marcia S Noble
(74) *Attorney, Agent, or Firm*—Sutherland Asbill & Brennan LLP

(57) ABSTRACT

The present invention provides compositions and methods for the culture and maintenance of cancer stem cells. More particularly, the present invention provides the identification of cancer stem cell specific markers and methods of recognizing the same for the detection of tumors, for facilitating the prognosis of a patient with a tumor, and for the treatment of various cancers. The invention also provides antibodies that specifically recognize the disulfide linked Erbb2Δ16 homodimer, an Erbb2Δ16/Erbb3 heterodimer, or post-translational modifications of Erbb2 that are specific to Erbb2 of variant hESCs. In addition, the invention provides a modified defined media useful in the absence of a feeder layer and in the absence of serum or serum replacement, that comprises a basal salt nutrient solution, bFGF, IGF-I, and Activin A, and wherein the composition does not comprise heregulin. The invention further relates to the use of an Erbb2 variant isoform to generate robust cell cultures that are independent of heregulin.

4 Claims, 11 Drawing Sheets

OTHER PUBLICATIONS

Mehta et al., 1998, "Plasma c-erbB-2 Levels in Breast Cancer Patients: Prognostic Significance in Predicting Response to Chemotherapy," Oncol., 16:2409-2416.

Menendez et al., 2004, "Inhibition of Fatty Acid Synthase (FAS) Suppresses HER2 / neu (erbB2) Oncogene Overexpression in Cancer Cells," Proc. Nat. Acad. Sci., 101:10715-10720.

Mitalipova et al., 2005, "Preserving the Genetic Integrity of Human Embryonic Stem Cells," Nat. Biotechnol. 23 (1):19-20.

Muleris et al., 1997, "Assignment of v-erb-b2 Avian Erythroblastic Leukemia viral Oncogene Homolog 2 (ERBB2) to Human Chromosome Band 17q21.1 by in situ Hybridization," Cytogenet. Cell Genet., 76:34-35.

Neve et al., 2001, "The Role of Overexpressed HER2 in Transformation," Ann. Oncol., 12 Suppl 1:S9-13.

Oda et al., 2005, "A Comprehensive Pathway Map of Epidermal Growth Factor Receptor Signaling," Mol. Sys. Biol., 1:2005.0010. Epub May 25.

Pegram et al., 1997, "The Effect of HER-2 / neu Overexpression on Chemotherapeutic Drug Sensitivity in Human Breast and Ovarian Cancer Cells," Oncogene, 15:537-547.

Semba et al., 1985, "A v-erbB-Related Protooncogene, c-erbB-2, is Distinct from the c-erbB-1 / Epidermal Growth Factor-Receptor Gene and is Amplified in a Human Salivary Gland Adenocarcinoma," Proc. Nat. Acad. Sci., 82:6497-6501.

Siegel et al., 1999, "Elevated Expression of Activated Forms of Neu/ErbB-2 and ErbB-3 are Involved in the Induction of Mammary Tumors in Transgenic Mice: Implications for Human Breast Cancer," EMBO J., 18(8):2149-64.

Toyoda-Ohno et al., 1999, "Members of the ErbB Receptor Tyrosine Kinases are Involved in Germ Cell Development in Fetal Mouse Gonads," Dev. Biol., 215(2):399-406).

Yarden, 2001, "Biology of HER2 and Its Importance in Breast Cancer," Oncology, 61 Suppl 2:1-13.

Yu et al., 1988, "Overexpression of ErbB2 Blocks Taxol-Induced Apoptosis by Upregulation of p21Cip1, which Inhibits p34Cdc2 Kinase," Mol. Cell, 2:581-591.

Yuan et al., 2003, Prot. Exp. Pur., 29:217-222.

Zhou et al., 2003, Dysregulation of Cellular Signaling by HER2/neu in Breast Cancer, Semin. Oncol., 30(5 Suppl 16):38-48.

Qiu et al., 1998, "Requirement of ErbB2 for Signaling by interleukin-6 in Prostate Carcinoma Cells," Nature 393:83-85.

Slamon et al., 1989, "Studies of the HER-2/neu Proto-Oncogene in Human Breast and Ovarian Cancer," Science, 244:707-712.

Sperger et al., 2003, "Gene Expression Patterns in Human Embryonic Stem Cells and Human Pluripotent Germ Cell Tumors," PNAS, 100(23):13350-13355.

Stojkovc et al., 2004, "Derivation, Growth, and Applications of Human Embryonic Stem Cells," Reproduction, 128:259-267.

Tan et al., 2002, "Phosphorylation on Tyrosine-15 of p34Cdc2 by ErbB2 inhibits p34Cdc2 Activation and is Involved in Resistance to Taxol-Induced Apoptosis," Mol. Cell, 9:993-1004.

Ulloa-Montoya et al., 2005, "Culture Systems for Pluripotent Stem Cells," J. Biosci. Bioengen., 100(1)12-27.

Van de Vijver et al., 1988, Neu-Protein Overexpression in Breast Cancer, Association with Comedo-Type Ductal Carcinoma in situ and Limited Prognostic Value in State II Breast Cancer, New Eng. J. Med., 319:1239-1245.

Xie et al., 2000, "Population-Based, Case-Control Study of HER2 Genetic Polymorphism and Breast Cancer Risk," J. Nat. Cancer Inst., 92:412-417.

Yang-Feng et al., 1985, "The Pronatriodilatin Gene is Located on the Distal Short Arm of Human Chromosome 1 and on Mouse Chromosome 4," Cytogenet. Cell Genet. 40:784.

* cited by examiner

FIG. 1

MELAALcRWGLLLALLPPGAASTQVcTGTDMKLRLPASPETHLDMLRHLYQGcQVVQGNLELTYLPT*NAS*
LSFLQDIQEVQGYVLIAHNQVRQVPLQRLRIVRGTQLFEDNYALAVLDNGDPL*NNTT*PVTGASPGGLREL
QLRSLTEILKGGVLIQRNPQLcYQDTILWKDIFHKNNQLALTLIDT*NRS*RAcHPcSPMcKGSRcWGESSE
DcQSLTRTVcAGGcARcKGPLPTDccHEQcAAGcTGPKHSDcLAcLHF*NHS*GIcELHcPALVTYNTDTFE
SMPNPEGRYTFGAScVTAcPYNYLSTDVGScTLVcPLHNQEVTAEDGTQRcEKcSKPcARVcYGLGMEHL
REVRAVTSANIQEFAGcKKIFGSLAFLPESFDGDPASNTAPLQPEQLQVFETLEEITGYLYISAWPDSLP
DLSVFQNLQVIRGRILHNGAYSLTLQGLGISWLGLRSLRELGSGLALIHHNTHLcFVHTVPWDQLFRNPH
QALLHTANRPEDEcVGEGLAcHQLcARGHcWGPGPTQcV*NcS*QFLRGQEcVEEcRVLQGLPREYVNARHc
LPcHPEcQPQ*NGS*VTcFGPEADQcVAcAHYKDPPFcVARcPSGVKPDLSYMPIWKFPDEEGAcQPcPI*Nc*
*THScVDLDDKGcPAEQRAS*PLTSIISAVVGILLVVVLGVVFGILIKRRQQKIRKYTMRRLLQETELVEPL
TPSGAMPNQAQMRILKETELRKVKVLGSGAFGTVYKGIWIPDGENVKIPVAIKVLRENTSPKANKEILDE
AYVMAGVGSPYVSRLLGIcLTSTVQLVTQLMPYGcLLDHVRENRGRLGSQDLLNWcMQIAKGMSYLEDVR
LVHRDLAARNVLVKSPNHVKITDFGcLARLLDIDETEYHADGGKVPIKWMALESILRRRFTHQSDVWSYGV
TVWELMTFGAKPYDGIPAREIPDLLEKGERLPQPPIcTIDVYMIMVKcWMIDSEcRPRFRELVSEFSRMA
RDPQRFVVIQNEDLGPASPLDSTFYRSLLEDDDMGDLVDAEEYLVPQQGFFcPDPAPGAGGMVHHRHRSS
STRSGGGDLTLGLEPSEEEAPRSPLAPSEGAGSDVFDGDLGMGAAKGLQSLPTHDPSPLQRYSEDPTVPL
PSETDGYVAPLTcSPQPEYVNQPDVRPQPPSPREGPLPAARPAGATLERPKTLSPGKNGVVKDVFAFGGA
VENPEYLTPQGGAAPQPHPPPAFSPAFDNLYYWDQDPPERGAPPSTFKGTPTAENPEYLGLDVPV

SEQ ID NO: 1

FIG. 2
A
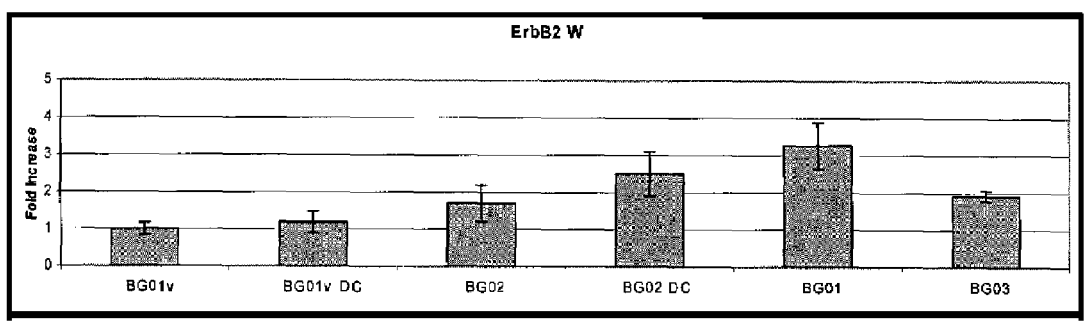
B
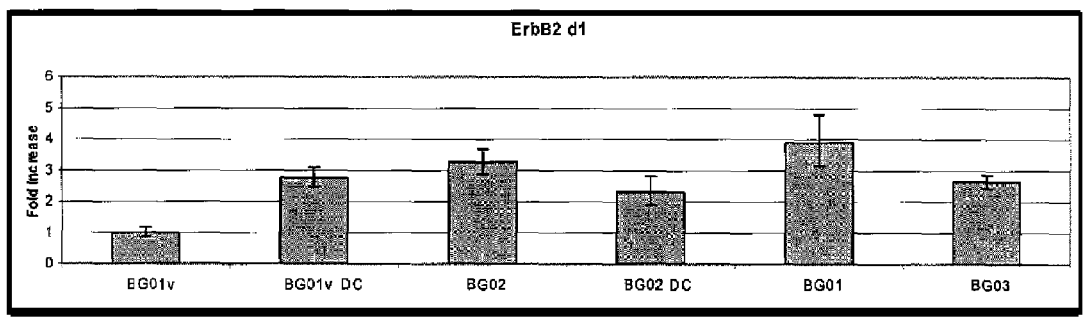
C
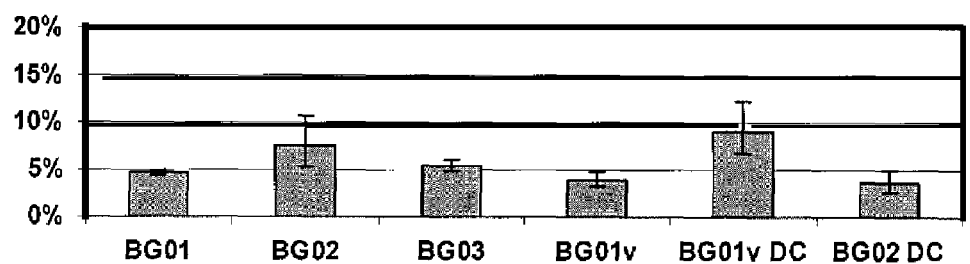

FIG. 6

```
1
GGAGGAGGTGGAGGACGAGGGCTGCTTGAGGAAGTATAAGAATGAAGTTGTGAAGCTGAGATTCCCCTCCATTGGGACCG

GAGAAACCAGGGCAGCCCCCCGGGCAGCCGCGCGCCCCTTCCCACGGGGCCCTTTACTGCGCCGCGCGCCCGGCCCCCACCCCTCGCAGCACCCCGC
GCCCCGCGCCCTCCCAGCCGGGTCCAGCCGGAGCCATGGGGCCGGAGCCGCAGTGAGCACCATGGAGCTGGCGGCCTTGTGCCGCTGGGGGCTCCTC
CTCGCCCTCTTGCCCCCCGGAGCCGCGAGCACCCAAGTGTGCACCGGCACAGACATGAAGCTGCGGCTCCCTGCCAGTCCCGAGACCCACCTGGACA
TGCTCCGCCACCTCTACCAGGGCTGCCAGGTCGTGCAGGGAAACCTGGAACTCACCTACCTGCCCACCAATGCCAGCCTGTCCTTCCTGCAGGATAT
CCAGGAGGTGCAGGGCTACGTGCTCATCGCTCACAACCAAGTGAGGCAGGTCCCACTGCAGAGGCTGCGGATTGTGCCAGGCACCCAGCTCTTTGAG
GACAACTATGCCCTGGCCGTGCTAGACAATGGAGACCCGCTGAACAATACCACCCCTGTCACAGGGGCCTCCCCAGGAGGCCTGCGGGAGCTGCAGC
TTCGAAGCCTCACAGAGATCTTGAAAGGAGGGGTCTTGATCCAGCGGAACCCCCAGCTCTGCTACCAGGACACGATTTTGTGGAAGGACATCTTCCA
CAAGAACAACCAGCTGGCTCTCACACTGATAGACACCAACCGCTCTCGGGCCTGCCACCCCTGTTCTCCGATGTGTAAGGGCTCCCGCTGCTGGGGA
GAGAGTTCTGAGGATTGTCAGAGCCTGACGCGCACTGTCTCGTGCCGGTGGCTGTGCCCGCTGCAAGGGGCCACTGCCCACTGACTGCTGCCATGAGC
AGTGTGCTGCCGGCTGCACGGGCCCCAAGCACTCTGACTGCCTGGCCTGCCTCCACTTCAACCACAGTGGCATCTGTGAGCTGCACTGCCCAGCCCT
GGTCACCTACAACACAGACACGTTTGAGTCCATGCCCAATCCCGAGGGCCGGTATACATTCGGCGCCAGCTGTGTGACTGCCTGTCCCTACAACTAC
CTTTCTACGGACGTGGGATCCTGCACCCTCGTCTGCCCCCTGCACAACCAAGAGGTGACAGCAGAGGATGGAACACAGCGGTGTGAGAAGTGCAGCA
AGCCCTGTGCCCGAGTGTGCTATGGTCTGGGCATGGAGCACTTGCGAGAGGTGAGGGCAGTTACCAGTGCCAATATCCAGGAGTTTGCTGGCTGCAA
GAAGATCTTTGGGAGCCTGGCATTTCTGCCGGAGAGCTTTGATGGGACCCAGCCTCCAACACTGCCCCGCTCCAGCCAGAGCAGCTCCAAGTGTTT
GAGACTCTGGAAGAGATCACAGGTTACCTATACATCTCAGCATGGCCGGACAGCCTGCCTGACCTCAGCGTCTTCCAGAACCTGCAAGTAATCCGGG
GACGAATTCTGCACAATGGCGCCTACTCGCTGACCCTGCAAGGGCTGGGCATCAGCTGGCTGGGGCTGCGCTCACTGAGGGAACTGGGCAGTGGACT
GGCCCTCATCCACCATAACACCCACCTCTGCTTCGTGCACACGGTGCCTGGGACCAGCTCTTTCGGAACCCGCACCAAGCTCTGCTCCACACTGCC
AACCGGCCAGAGGACGAGTGTGTGGGCGAGGGCCTGGCCTGCCACCAGCTGTGCGCCCGAGGGCACTGCTGGGGTCCAGGGCCCACCCAGTGTGTCA
ACTGCAGCCAGTTCCTTCGGGGCCAGGAGTGCGTGGAGGAATGCCGAGTACTGCAGGGGCTCCCCAGGGAGTATGTGAATGCCAGGCACTGTTTGCC
GTGCCACCCTGAGTGTCAGCCCCAGAATGGCTCAGTGACCTGTTTTGGACCGGAGGCTGACCAGTGTGTGGCCTGTGCCCACTATAAGGACCCTCCC
TTCTGCGTGGCCCGCTGCCCCAGCGGTGTGAAACCTGACCTCTCCTACATGCCCCATCTGGAAGTTTCCAGATGAGGAGGGCGCATGCCAGCCTTGCC
*CCATCAACTGCACCCACTCCCCTCTGACGTCCATCATCTCTGCGGTGGTTGGCATTCTGCTGGTCGTGGTCTTGGGGGTGGTCTTTGGGATCCTCA
TCAAGCGACGGCAGCAGAAGATCCGGAAGTACACGATGCGGAGACTGCTGCAGGAAACGGAGCTGGTGGAGCCGCTGACACCTAGCGGAGCGATGCC
CAACCAGGCGCAGATGCGGATCCTGAAAGAGACGGAGCTGAGGAAGGTGAAGGTGCTTGGATCTGGCGCTTTTGGCACAGTCTACAAGGGCATCTGG
ATCCCTGATGGGGAGAATATTCCAGTGGCCATCAAAGTGTTGAGGAGGTGAGGGAAACACATCCCCCAAAGCCAACAAAGAAATCTTAGACGAAGCAT
ACGTGATGGCTGGTGTGGGCTCCCCATATGTCTCCCGCCTTCTGGGCATCTGCCTGACATCCACGGTGCAGCTGGTGACACAGCTTATGCCCTATGG
CTGCCTCTTAGACCATGTCCGGGAAAACCGCGGACGCCTGGGCTCCCAGGACCTGCTGAACTGGTGTATGCAGATTGCCAAGGGGATGAGCTACCTG
GAGGATGTGCGGCTCGTACACAGGGACTTGGCCGCTCGGAACGTGCTGGTCAAGAGTCCCAACCATGTCAAAATTACAGACTTCGGGCTGGCTCGGC
TGCTGGACATTGACGAGACAGAGTACCATGCAGATGGGGGCAAGGTGCCCATCAAGTGGATGGCGCTGGAGTCCATTCTCCGCCGGCGTTCACCCA
CCAGAGTGATGTGTGGAGTTATGGTGTGACTGTGTGGGAGCTGATGACTTTTGGGGCCAAACCTTACGATGGGATCCCAGCCCGGGAGATCCCTGAC
CTGCTGGAAAAGGGGGAGCGGCTGCCCCAGCCCCCATCTGCACCATTGATGCTACATGATCATGGTCAAATGTTGGATGATTGACTCTGAATGTC
GGCCAAGATTCCGGGAGTTGGTGTCTGAATTCTCCCGCATGGCCAGGGACCCCCAGCGCTTTGTGGTCATCCAGAATGAGGACTTGGGCCCAGCCAG
TCCCTTGGACAGCACCTTCTACCGCTCACTGCTGGAGGACGATGACATGGGGGACCTGGTGGATGCTGAGGAGTATCTGGTACCCCAGCAGGGCTTC
TTCTGTCCAGACCCTGCCCCGGCGCTGGGGGCATGGTCCACCACAGGCACCGCAGCTCATCTACCAGGAGTGGCGTGGGGACCTGACACTAGGGC
TGGAGCCCTCTGAAGAGGAGGCCCCCAGGTCTCCACTGGCACCCTCCGAAGGGGCTGGCTCCGATGTATTTGATGGTGACCTGGGAATGGGGGCAGC
CAAGGGGCTGCAAAGCCTCCCCACACATGACCCCAGCCCTCTACAGCGGTACAGTGAGGACCCCACAGTACCCCTGCCCTCTGAGACTGATGGCTAC
GTTGCCCCCCTGACCTGCAGCCCCAGCCTGAATATGTGAACCAGCCAGATGTTCGGCCCCAGCCCCCTTCGCCCCGAGAGGGCCCTCTGCCTGCTG
CCCGACCTGCTGGTGCCACTCTGGAAAGGGCCAAGACTCTCTCCCCAGGGAAGAATGGGGTCGTCAAAGACGTTTTGCCTTTGGGGGTGCCGTGGA
GAACCCCGAGTACTTGACACCCCAGGGAGGAGCTGCCCCTCAGCCCCACCCTCCTCCTGCCCTTCAGCCCAGCCTTCGACAACCTCTATTACTGGGAC
CAGGACCCACCAGAGCGGGGGGCTCCACCCAGCACCTTCAAAGGACACCTACGCAGAGAACCCAGAGTACCTGGGCTGGACGTGCCAGTGTGAA
CCAGAAGGCCAAGTCCGCAGAAGCCCTGATGTGTCCTCAGGGAGCAGGGAAGGCCTGACTTCTGCTGGCATCAAGAGGTGGGAGGGCCCTCCGACCA
CTTCCAGGGGAACCTGCCATGCCAGGAACCTGTCCTAAGGAACCTTCCTTCCTGCTTGAGTTCCCAGATGGCTGGAAGGGGTCCAGCCTCCTTCGGAA
GAGGAACAGCACTGGGGAGTCTTTGTGGATTCTGAGGCCCTGCCCAATGAGACTCTAGCGTCCAGTGGATGCCACAGCCCACCTTGGCCCTTTCCTT
CCAGATCCTGGGTACTGAAAAGCCTTAGGGAAGCTGGCCTGAGAGGGGAAGCGGCCCTAAGGGAGTGTCTAAGAACAAAAGCGACCCATTCAGACACT
GTCCCTGAAACCTAGTACTGCCCCCATGAGGAAGGAACACCAATGGTGTCAGTATCCAGGCTTTGTACAGAGTGCTTTTCTGTTTAGTTTTACTT
TTTTTGTTTGTTTTTTAAAGATGAAATAAAGACCCAGGGGAGAATG

GGTGTTGTATGGGGAGGCAAGTGTGGGGGGTCCTTCTCCACACCCACTTTGTCCATTTGCAAATATATTTTGGAAAACAGCTA

SEQ ID NO: 2
```

SEQ ID NO: 3
```

FIG. 8

```
D16,        1  MELAALCRWGLLLALLPPGAASTQVCTGTDMKLRLPASPETHLDMLRHLYQGCQVVQGNL
Erbb2a,     1  MELAALCRWGLLLALLPPGAASTQVCTGTDMKLRLPASPETHLDMLRHLYQGCQVVQGNL
               ************************************************************

D16,       61  ELTYLPTNASLSFLQDIQEVQGYVLIAHNQVRQVPLQRLRIVRGTQLFEDNYALAVLDNG
Erbb2a,    61  ELTYLPTNASLSFLQDIQEVQGYVLIAHNQVRQVPLQRLRIVRGTQLFEDNYALAVLDNG
               ************************************************************

D16,      121  DPLNNTTPVTGASPGGLRELQLRSLTEILKGGVLIQRNPQLCYQDTILWKDIFHKNNQLA
Erbb2a,   121  DPLNNTTPVTGASPGGLRELQLRSLTEILKGGVLIQRNPQLCYQDTILWKDIFHKNNQLA
               ************************************************************

D16,      181  LTLIDTNRSRACHPCSPMCKGSRCWGESSEDCQSLTRTVCAGGCARCKGPLPTDCCHEQC
Erbb2a,   181  LTLIDTNRSRACHPCSPMCKGSRCWGESSEDCQSLTRTVCAGGCARCKGPLPTDCCHEQC
               ************************************************************

D16,      241  AAGCTGPKHSDCLACLHFNHSGICELHCPALVTYNTDTFESMPNPEGRYTFGASCVTACP
Erbb2a,   241  AAGCTGPKHSDCLACLHFNHSGICELHCPALVTYNTDTFESMPNPEGRYTFGASCVTACP
               ************************************************************

D16,      301  YNYLSTDVGSCTLVCPLHNQEVTAEDGTQRCEKCSKPCARVCYGLGMEHLREVRAVTSAN
Erbb2a,   301  YNYLSTDVGSCTLVCPLHNQEVTAEDGTQRCEKCSKPCARVCYGLGMEHLREVRAVTSAN
               ************************************************************

D16,      361  IQEFAGCKKIFGSLAFLPESFDGDPASNTAPLQPEQLQVFETLEEITGYLYISAWPDSLP
Erbb2a,   361  IQEFAGCKKIFGSLAFLPESFDGDPASNTAPLQPEQLQVFETLEEITGYLYISAWPDSLP
               ************************************************************

D16,      421  DLSVFQNLQVIRGRILHNGAYSLTLQGLGISWLGLRSLRELGSGLALIHHNTHLCFVHTV
Erbb2a,   421  DLSVFQNLQVIRGRILHNGAYSLTLQGLGISWLGLRSLRELGSGLALIHHNTHLCFVHTV
               ************************************************************

D16,      481  PWDQLFRNPHQALLHTANRPEDECVGEGLACHQLCARGHCWGPGPTQCVNCSQFLRGQEC
Erbb2a,   481  PWDQLFRNPHQALLHTANRPEDECVGEGLACHQLCARGHCWGPGPTQCVNCSQFLRGQEC
               ************************************************************

D16,      541  VEECRVLQGLPREYVNARHCLPCHPECQPQNGSVTCFGPEADQCVACAHYKDPPFCVARC
Erbb2a,   541  VEECRVLQGLPREYVNARHCLPCHPECQPQNGSVTCFGPEADQCVACAHYKDPPFCVARC
               ************************************************************

D16,      601  PSGVKPDLSYMPIWKFPDEEGACQPCPINCTHS----------------PLTSIISAVVG
Erbb2a,   601  PSGVKPDLSYMPIWKFPDEEGACQPCPINCTHS*CVDLDDKGCPAEQRAS*PLTSIISAVVG
               ********************************                **********

D16,      645  ILLVVVLGVVFGILIKRRQQKIRKYTMRRLLQETELVEPLTPSGAMPNQAQMRILKETEL
Erbb2a,   661  ILLVVVLGVVFGILIKRRQQKIRKYTMRRLLQETELVEPLTPSGAMPNQAQMRILKETEL
               ************************************************************

D16,      705  RKVKVLGSGAFGTVYKGIWIPDGENVKIPVAIKVLRENTSPKANKEILDEAYVMAGVGSP
Erbb2a,   721  RKVKVLGSGAFGTVYKGIWIPDGENVKIPVAIKVLRENTSPKANKEILDEAYVMAGVGSP
               ************************************************************
```

FIG. 8 Continued

```
D16,    765  YVSRLLGICLTSTVQLVTQLMPYGCLLDHVRENRGRLGSQDLLNWCMQIAKGMSYLEDVR
Erbb2a, 781  YVSRLLGICLTSTVQLVTQLMPYGCLLDHVRENRGRLGSQDLLNWCMQIAKGMSYLEDVR
             ************************************************************

D16,    825  LVHRDLAARNVLVKSPNHVKITDFGLARLLDIDETEYHADGGKVPIKWMALESILRRRFT
Erbb2a, 841  LVHRDLAARNVLVKSPNHVKITDFGLARLLDIDETEYHADGGKVPIKWMALESILRRRFT
             ************************************************************

D16,    885  HQSDVWSYGVTVWELMTFGAKPYDGIPAREIPDLLEKGERLPQPPICTIDVYMIMVKCWM
Erbb2a, 901  HQSDVWSYGVTVWELMTFGAKPYDGIPAREIPDLLEKGERLPQPPICTIDVYMIMVKCWM
             ************************************************************

D16,    945  IDSECRPRFRELVSEFSRMARDPQRFVVIQNEDLGPASPLDSTFYRSLLEDDDMGDLVDA
Erbb2a, 961  IDSECRPRFRELVSEFSRMARDPQRFVVIQNEDLGPASPLDSTFYRSLLEDDDMGDLVDA
             ************************************************************

D16,    1005 EEYLVPQQGFFCPDPAPGAGGMVHHRHRSSSTRSGGGDLTLGLEPSEEEAPRSPLAPSEG
Erbb2a, 1021 EEYLVPQQGFFCPDPAPGAGGMVHHRHRSSSTRSGGGDLTLGLEPSEEEAPRSPLAPSEG
             ************************************************************

D16,    1065 AGSDVFDGDLGMGAAKGLQSLPTHDPSPLQRYSEDPTVPLPSETDGYVAPLTCSPQPEYV
Erbb2a, 1081 AGSDVFDGDLGMGAAKGLQSLPTHDPSPLQRYSEDPTVPLPSETDGYVAPLTCSPQPEYV
             ************************************************************

D16,    1125 NQPDVRPQPPSPREGPLPAARPAGATLERAKTLSPGKNGVVKDVFAFGGAVENPEYLTPQ
Erbb2a, 1141 NQPDVRPQPPSPREGPLPAARPAGATLERPKTLSPGKNGVVKDVFAFGGAVENPEYLTPQ
             ***************************** ******************************

D16,    1185 GGAAPQPHPPPAFSPAFDNLYYWDQDPPERGAPPSTFKGTPTAENPEYLGLDVPV
Erbb2a, 1201 GGAAPQPHPPPAFSPAFDNLYYWDQDPPERGAPPSTFKGTPTAENPEYLGLDVPV
             ******************************************************
```

D16 = SEQ ID NO:3
Erbb2a = SEQ ID NO:1

Fig. 9
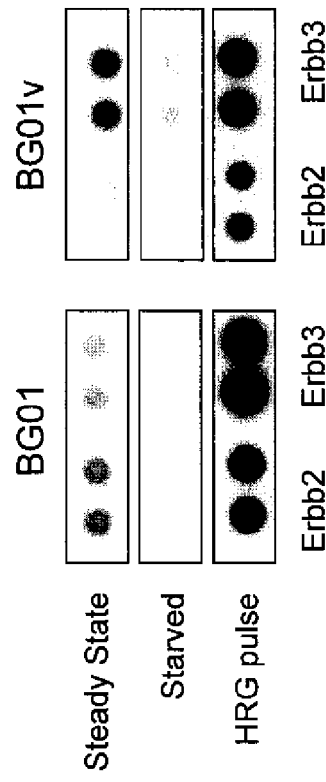
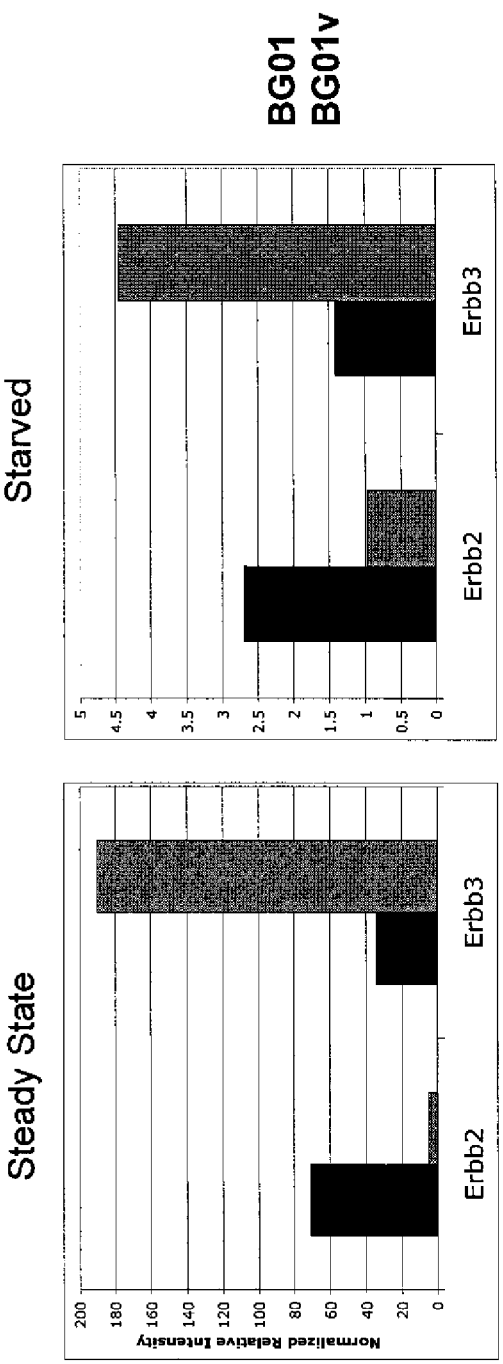
A
B

HUMAN CANCER STEM CELL CULTURE COMPOSITIONS COMPRISING ERBB2 VARIANTS AND METHODS OF USE THEREOF

CROSS REFERENCE TO RELATED APPLICATION(S)

This application claims the benefit of priority under 35 U.S.C. § 119(e) of U.S. Application Ser. No. 60/805,039 filed Jun. 16, 2006. The disclosure of that application is considered part of and is incorporated by reference in the disclosure of this application.

ACKNOWLEDGMENT OF FEDERAL RESEARCH SUPPORT

This invention was made, at least in part, with finding from NCRR (5R24RR021313-05). Accordingly, the United States Government has certain rights in this invention.

BACKGROUND OF THE INVENTION

1. Field of the Invention

The present invention generally relates to compositions and methods for culturing pluripotent stem cells and/or primary tumor cells comprising an Erbb2 variant, the cells created by these methods, and the uses thereof. Particularly, the invention relates to the identification of cancer stem cell specific markers. In addition, the invention relates to the use of a modified defined culture medium for producing cultures of cancer stem cells in the absence of a feeder cell layer, in the absence of serum or serum replacement, and independent of heregulin.

2. Background Art

The process of embryonic development establishes the differentiated lineages of the body and sets aside tissue specific progenitor cells, which are also called stem cells. These progenitor cells are capable of regenerating all the relevant lineages of individual tissues during normal cellular turnover, or after injury. Examples of this regeneration include the constant regeneration of the skin, and reconstitution of the hematopoetic system following transplantation of hematopoetic stem cells. These progenitor cells typically reside in a "stem cell niche" and are relatively long lived as compared to their differentiated progeny. Embryonic stem (ES) cells represent a powerful model system for the investigation of mechanisms underlying pluripotent cell biology and differentiation within the early embryo, as well as providing opportunities for genetic manipulation of mammals and resultant commercial, medical, and agricultural applications. Furthermore, appropriate proliferation and differentiation of ES cells can be used to generate an unlimited source of cells suited to study cell differentiation and/or suited for transplantation for treatment of diseases that result from cell damage or dysfunction.

Accumulated genetic change leading to unregulated cell growth is a hallmark of cancer progression. Because of their longevity, tissue specific stem cells may have a greater chance of accumulating mutations than differentiated cells, which exhibit comparatively rapid turnover in many tissues. Because tissue specific stem cells are the progenitor cells of other cells within that tissue, deregulation of the balance between quiescence, self-renewal, differentiation, or apoptosis of the tissue specific stem cells can have severe consequences. Any increase in the proliferation of these cells could lead to a magnified over-proliferation of downstream cell populations, leading to tumorigenesis. Furthermore, should mutations enable maintenance or expansion of these progenitor cells, self-perpetuating "cancer stem cells" (CSC) could be generated within tumors. It has long been known that a relatively small proportion of cells within differentiated tumors have the capacity to regenerate tumors at high frequency after transplantation (See, e.g., U.S. Pat. No. 6,984, 522). This is indicative of rare populations of transformed cells that have the capacity to expand and differentiate to all lineages of the tumor. There is a need in the art for a natural model system in which to study the development of and signaling within a cancer stem cell population.

Human embryonic stem cells (hESCs) are pluripotent cells that can be isolated from the human blastocyst and maintained in culture as self-renewing cells, or differentiated to representatives of all mature tissues in the body. hESCs may therefore be a valuable model of human development in vitro, and are the focus of substantial research aimed at generating differentiated populations for cellular therapies. hESCs are "master" stem cells and theoretically capable of differentiating to all lineages, including tissue specific progenitor cells. Because hESCs are a self-renewing progenitor population, they are likely to use growth factors and molecular signaling pathways that are overlapping with some tissue specific stem cells and their related CSCs.

The successful isolation, long-term clonal maintenance, genetic manipulation, and germ-line transmission of pluripotent cells has generally been difficult, and the biochemical mechanisms regulating ES cell pluripotency and differentiation are very poorly understood. However, the limited empirical data available and much anecdotal evidence suggest that the continued maintenance of pluripotent ES cells under in vitro culture conditions is dependent upon the presence of cytokines and growth factors present in the extracellular milieu. Until recently, the standard growth conditions for hESCs were relatively undefined. The inventors recently developed a simple media for HESC growth that has several advantages over other reported defined media. The media relies on growth factor signaling through the EGF receptor family of cell surface proteins to maintain hESC pluripotency. This signaling is primarily transmitted through the Erbb2 receptor, a strong activator of the PI3 kinase pathway when present as heterodimers with other Erbb receptor family members. Four growth factors (bFGF, TGF-I, Activin A, and Heregulin) were required to inhibit spontaneous differentiation and promote self renewal of hESCs in this defined media. This system enabled the robust expansion of hFSCs and facilitated the examination of such cells in a standardized and simple background.

Neuregulin-1 (NRG1; heregulin) is a large gene that exhibits multiple splicing and protein processing variants. This generates a large number of protein isoforms, which are referred to herein collectively as neuregulin. Neuregulin is predominantly expressed as a cell surface transmembrane protein. The extracellular region contains an immunoglobulin-like domain, a carbohydrate modified region and the EGF domain. NRG1 expression isoforms have been reviewed previously (Falls, 2003, Exp. Cell Res., 284:14-30). The cell membrane metalloproteases ADAM17 and ADAM19 have been shown to process the transmembrane form(s) of neuregulin-1 to soluble neuregulin/heregulin. HRG-α and -β are the cleaved ectodomains of neuregulin, containing the EGF and other domains. As the EGF domain is responsible for binding and activation of the Erbb receptors, a recombinant molecule containing only this domain can exhibit essentially all of the soluble growth factor effects of this protein (Jones et al., 1999, FEBS Lett., 447:227-231). Also, there are processed transmembrane isoforms of neuregulin that are thought to trigger juxtacrine signaling in adjacent cells via interaction of the EGF domain with Erbb receptors.

The EGF growth factor family has at least 14 members, including, but not limited to, EGF, TGFα, heparin binding-EGF (hb-EGF), neuregulin-β (also named heregulin-β (HRG-β), glial growth factor and others), HRG-α, amphiregulin, betacellulin, and epiregulin. All these growth factors contain an EGF domain and are typically first expressed as transmembrane proteins that are processed by metalloproteinase (specifically, ADAMs) proteins to generate soluble ectodomain growth factors. EGF family members interact with both homo- and hetero-dimers of the Erbb1, 2, 3, and 4 cell surface receptors with different affinities (Jones et at, 1999, FEBS Lett, 447:227-231). EGF, TGFα, and hbEGF bind Erbb1/1 (EGFR) homodimers and Erbb1/2 heterodimers at high affinity (1-100 nM range), whereas HRG-β binds Erbb2/3 and Erbb2/4 heterodimers at very high affinity (<1 nM range). Activated Erbb receptors signal through the PI3 Kinase/AKT pathway, the MAPK pathway, and several other pathways (Oda et al., 2005, Mol. Sys. Biol., 1:2005.0010. Epub May 25).

Erbb2 and Erbb3 are amongst the most highly expressed growth factor receptors in hESCs (Sperger et al., 2003, PNAS, 100(23):13350-13355), and HRG-β has been shown previously to support the expansion of mouse primordial germ cells (Toyoda-Ohno et al., 1999, Dev. Biol., 215(2):399-406). Furthermore, over-expression and subsequent inappropriate activation of Erbb2 is associated with tumorigenesis (Neve et al., 2001, Ann. Oncol., 12 Suppl 1:S9-13; Zhou & Hung, 2003, Semin. Oncol., 30(5 Suppl 16):38-48; Yarden, 2001, Oncology, 61 Suppl 2:1-13). Human Erbb2 (Chromosome 17q between positions 11.2 and 12), and Erbb3 (Chromosome 12q13) are present on chromosomes that have been observed to accumulate as trisomies in some hESCs (Draper et al., 2004, Nat. Biotechnol., 22(1):53-4; Cowan et al., 2004, N Engl. J. Med., 350(13):1353-6; Brimble et al., 2004, Stem Cells Dev., 13(6):585-97; Maitra et al., 2005, Nat. Genet., 37(10):1099-103; Mitalipova et al., 2005, Nat. Biotechnol., 23(1):19-20; Draper et al., 2004, Stem Cells Dev., 13(4):325-36; Ludwig et al., 2006, Nature Biotechnol., 24(2):185-87), possibly suggesting that over-expression and/or activation of these receptors could be associated with the purported growth/survival advantage conferred by trisomies of these chromosomes.

The proto-oncogene Erbb2 is known in the art by several additional names, including, among others, human epidermal growth factor receptor 2 (HER2), C-erbB-2, ERB2_HUMAN, Her-2/neu, MLN 19, NEU, NEU proto-oncogene, NGL, Oncogene NGL, neuroblastoma- or glioblastoma-derived, p185erbB2, TKR1, Tyrosine kinase-type cell surface receptor HER2, V-Erb-B2, and Oncogene Erbb2. Various groups identified the genes and/or mapped the location to the long arm q of Chromosome 17 (Coussens et al., 1985, Science, 230:1132-1139; Semba et al., 1985, Proc. Nat. Acad. Sci., 82:6497-6501; Yang-Feng et al., 1985, Cytogenet. Cell Genet., 40:784; Di Fiore et al., 1987, Science, 237:178-182; Fukushige et al., 1986, Mol. Cell. Biol., 6:955-958; Kaneko et al., 1987, Jpn. J. Cancer Res., 78:16-19; Popescu et alt, 1989, Genomics, 4:362-366; Anderson et al., 1993, Genomics, 17:618-623; Muleris et al., 1997, Cytogenet. Cell Genet., 76:34-35). The Erbb2 gene consists of 27 exons, and the mRNA is approximately 3,768 nucleotides. Akiyama et al. (1986, Science 232:1644-46) raised antibodies against a synthetic peptide corresponding to 14 amino acid residues at the COOH terminus of the predicted Erbb2 protein, and they immunoprecipitated an 185-kD Erbb2 glycoprotein with tyrosine kinase activity from adenocarcinoma cells. The Erbb2 protein consists of 1255 amino acids. Erbb2 is a tyrosine kinase with a single transmembrane domain that separates an intracellular kinase domain from an extracellular domain. Erbb2 protein is expressed in several human organs and tissues, including normal epithelium, endometrium, ovarian epithelium, prostate, pancreas, lung, kidney, liver, heart, and hematopoietic cells. Erbb2 plays a role in normal development and differentiation.

Several researchers have identified the over-expression of Erbb2 as being involved in various cancers and have analyzed Erbb2's role as an oncogene. For example, increased expression of Erbb2 was noted in a human adenocarcinoma of the salivary gland (Semba et al., 1985, Proc. Nat. Acad. Sci., 82:6497-6501), a gastric cancer cell line (Fukushige et al., 1986, Mol. Cell. Biol., 6:955-958), a large-cell, comedo growth type of ductal carcinoma (Van de Vijver et al., 1988, New Eng. J. Med., 319:1239-1245), breast and ovarian cancer (Slamon et al., 1989, Science, 244:707-71 2; Yu et al., 1998, Mol. Cell, 2:581-591; Kun et al., 2003, Hum. Mol. Genet. 12:3245-3258; Menendez et al., 2004, Proc. Nat. Acad. Sci., 101:10715-10720), prostate cancer (Qiu et al., 1998, Nature, 393:83-85), acute lymphoblastic leukemia, bladder cancer, cervical cancer, childhood medulloblastoma, colorectal cancer, oral squamous cell carcinoma, germ-cell testicular cancer, cholangiocarcinoma, lung cancer, osteosarcoma, pancreatic adenocarcinoma, primary fallopian tube carcinoma, and synovial sarcoma. Di Fiore et al. (1987, Science, 237:178-182) demonstrated that over-expression alone can convert the Erbb2 gene into an oncogene. Other researchers have suggested that levels of Erbb2 expression could be used in determining the prognosis and/or chemosensitivity of human cancers, especially breast and ovarian cancer (Pegram et al., 1997, Oncogene, 15:537-547; Mehta et al., 1998, Oncol., 16:2409-2416; De Placido et al., 1998, Breast Cancer Res. Treat., 52:55-64). Erbb2 over-expression has been reported in 30-50% of ovarian carcinomas and is associated with advanced disease stage, worse prognosis, and decreased response to therapy in ovarian carcinoma patients; however, the molecular mechanisms underlying Erbb2 oncogenic activities in human cancer are unclear. Erbb2 over-expression is thought to be the mechanism of Erbb2 activation in certain cancers.

Other researchers have attempted to elucidate the function and activity of Erbb2. Qiu et al. (1998, Nature, 393:83-85) showed that Erbb2 forms a complex with the gp130 subunit of the IL6 receptor (IL6R) in an IL6-dependent manner and that Erbb2 is a critical component of IL6 signaling through the MAP kinase pathway. Yu et al. (1998, Mol. Cell, 2:581-591) found that over-expression of Erbb2 inhibits Taxol-induced apoptosis in breast cancers. The resistance to taxol-induced apoptosis is thought to be through the inhibition of p34 (CDC2) activation, via Erbb2-mediated upregulation of p21 (CIP1), or CDKN1A, which inhibits CDC2. Tan et al. (2002, Mol. Cell, 9:993-1004) reported that the inhibitory phosphorylation on tyr15 (Y15) of CDC2 was elevated in Erbb2-overexpressing breast cancer cells and primary tumors, and concluded that Erbb2 can confer resistance to taxol-induced apoptosis by directly phosphorylating CDC2. In addition, Menendez et al. (2004, Proc. Nat. Acad. Sci., 101:10715-10720) identified a molecular link between the biosynthetic enzyme fatty acid synthase (FASN), which is associated with more aggressive breast and ovarian cancers, and the Erbb2 oncogene. Pharmacologic and RNAi FASN inhibitors were found to suppress Erbb2 expression and tyrosine kinase activity in breast and ovarian cancers over-expressing Erbb2.

Certain mutations and polymorphisms in the Erbb2 protein have been identified as having an association with breast cancer, adenocarcinoma, glioblastoma, gastric cancer, and ovarian carcinoma (die et al., 2000, J. Nat. Cancer Inst., 92:412-417; The Cancer Genome Project and Collaborative Group, 2004). Alternative splicing results in several additional transcript variants, some encoding different isoforms and others that have not been fully characterized. Doherty et al. (1999, Proc. Nat. Acad. Sci., 96:10869-10874) described a secreted protein of approximately 68 kDa, designated herstatin, as the product of an alternative Erbb2 transcript that retains intron 8. Herstatin appears to be an inhibitor of p185Erbb2, because it disrupts dimers, reduces tyrosine phosphorylation of p185, and inhibits the anchorage-independent growth of transformed cells that over-express Erbb2.

Another Erbb2 splice variant (referred to here as Erbb2Δ16) has been identified which harbors a deletion of exon 16, resulting in a 16 amino acid in-frame deletion in a small extracellular region of wild type Erbb2 (Siegel et al., 1999, EMBO J., 18(8):2149-64; Castiglioni et al., 2006, Endocr. Relat. Cancer, 13(1):221-32). Erbb2Δ16 has been implicated as an oncogeneic isoform of Erbb2. Exon 16 also contains a cleavage site for ectodomain shedding of wild type Erbb2 (Yuan et al., 2003, Prot. Exp. Pur., 29:217:222), and shedding may, therefore, be substantially altered in Erbb2Δ16. Exon 16 also contains two cysteine residues that are usually involved in disulfide bonds with other regions of the molecule, and Erbb2Δ16 may therefore have a different structure than wild type Erbb2. Disulfide linked homodimers and/or heterodimers of Erbb2Δ16 may form in cells transfected with an Erbb2Δ16 expression construct. The region of the deletion in Erbb2Δ16 is also a hotspot for mutations in Erbb2 that lead to breast cancer in mouse and rat models. Some researchers have reported that this oncogenic Erbb2 splice variant has been detected in several breast cancer cell lines, but was not over-expressed in breast tumors.

Brumlik et al. (Poster, 2003, Faseb Summer Research Conference: Growth Factor Receptor Tyrosine Kinases in Mitogenesis. Omni-Tucson, Tucson, Ariz.) developed an RT-PCR assay to quantitate Erbb2Δ16 expression and have generated preliminary data that identified over-expression of Erbb2Δ16 in ovarian and breast cancer cell lines and primary ovarian tumors from patients with advanced disease, suggesting that Erbb2Δ16 may in fact contribute to disease progression and would therefore represent a viable target for therapeutic intervention of ovarian cancer. In addition, this group targeted a unique sequence at the Erbb2Δ16 exon 15 and exon 17 junction for suppression by RNA interference (RNAi) and demonstrated the efficacy and specificity of RNAi to suppress Erbb2Δ16 expression in ovarian cancer cells.

Similarly, Castiglioni et al. (2006, Endocrine Related Cancer, 13:221-232) have reported that the Erbb2Δ16 splice variant represents about 9% of the Erbb2 mRNA obtained from most of the 46 breast carcinoma samples in that study. They found that human cells transfected with wild type Erbb2 cDNA revealed no growth of wild type cells in nude mice, whereas clones expressing 10-fold less Erbb2Δ16 were tumorigenic. In addition, they noted that unlike wild type Erbb2-transfectants, Erbb2Δ16-expressing cells showed low sensitivity to two therapeutic drugs targeting receptors of the HER family (ZD1839 and Trastuzumab (Herceptin®)), whereas an inhibitor of the HER2 tyrosine kinase domain (Emodin) blocked activation of both Erbb2Δ16 and wild type Erbb2 transfectants. They suggested that their data indicate that the Erbb2Δ16 transcript encodes the transforming form of the oncoprotein and that malignant transformation arises when a critical threshold of Erbb2Δ16 is reached in Erbb2 over-expressing tumors.

Therapies directed toward Erbb2 are currently being used effectively in breast cancer patients; however, these treatments have significant drawbacks. In particular, a humanized anti-Erbb2 monoclonal antibody, Herceptin® (Genentech), has been shown to be effective in slowing the progression of approximately 30% of breast cancers, demonstrating the role of this receptor in tumor growth. Slamon et al. (2001, Science, 244:707-712) found in a large-scale clinical trial that treatment with Herceptin® increased the clinical benefit of first-line chemotherapy in metastatic breast cancer that over-expresses Erbb2. Although Hercepti® demonstrated clinical efficacy, a significant number of women suffered from the severe side effect of treatment-induced cardiotoxicity.

In addition, small molecule inhibitors of the Erbb2 tyrosine kinase (TK) domain have been shown to effectively inhibit proliferation of breast cancer cells in culture and in animal models of tumor growth. The inventors also have shown that three different Erbb2 TK inhibitors, AG879, AG825, and emodin, inhibit the growth of BG01v cells in defined media, in the absence of an exogenous Erbb2 activating growth factor. This confirms that endogenous Erbb2 signaling is critical for the self-renewal of BG01v cells and represents a major difference between variant and normal hESCs.

What is needed in the art are model systems for studying the transformation of tissue progenitor cells to cancer stem cells and the elucidation of media and cell culture conditions that are capable of effecting such transformation. Also needed are new methods for the specific targeted treatment of breast cancer and other tumors. There is a need, therefore, to identify methods and compositions for the culture of a population of cancer stem cells that are able to be used for research purposes to study tumorigenesis. There is also a need to identify markers that are specific to the cancer stem cells that may be used as targets for therapeutic treatments of cancer and that may be used to facilitate the prognosis of patients with various tumors.

SUMMARY OF THE INVENTION

It is an object of the present invention to overcome, or at least alleviate, one or more of the difficulties or deficiencies associated with the prior art. The present invention provides that ES cells and variant ES cells may be used to model very early transformation events that happen to tissue stem cells (i.e. changes to hChr17 and Erbb2). As disclosed herein, BG01 variant cells ("BG01v") can grow in a defined culture media independent of heregulin, and provide a good model to study early transformation events.

The present invention provides that BG01v ES cells express both wild type Erbb2 mRNA and an Erbb2 variant (Erbb2Δ16) mRNA, but that these cells predominantly express an Erbb2 variant isoform or an Erbb2 protein with a change in its post-translational modifications. Accordingly, the present invention discloses that trisomy of chromosome 17 in hESCs, which is associated with self-renewal that is independent of heregulin, is not associated with over-expression of an Erbb2 transcript. Rather, this growth factor independence of variant hESCs correlates with the post-transcriptional control of an Erbb2 transcript (e.g. differential splicing of an Erbb2 transcript) or the post-translational control of an Erbb2 protein (e.g. differential N-linked glycosylation of an Erbb2 protein).

Different Erbb2 protein isoforms have been identified in variant hESCs by differences in migration patterns on polyacrylamide gels. The present invention discloses that these differences in migration patterns of Erbb2 isoforms are likely caused by differences in N-linked glycosylation of the proteins. As shown herein, after deglycosylation of the protein isoforms, the migration pattern of the Erbb2 isoforms appeared to be the same in normal and variant hESCs. Accordingly, the differences in Erbb2 isoforms between normal and variant hESCs are targets for therapeutic agents and can be used, for example with antibodies, to specifically recognize cancer stem cells (CSCs) and to specifically treat tumors.

The present invention also provides an antibody which specifically binds to an Erbb2 receptor that has a mutation in the region of Exon 15 to Exon 17 of Erbb2 (or to an Erbb2 isoform that differs in its glycosylation profile from a wild type Erbb2 isoform). In a preferred embodiment, the antibody specifically binds an Erbb2Δ16 receptor. In certain embodiments, the antibody specifically recognizes a difference in post-translational modification of the Erbb2Δ16 receptor as compared to the wild type Erbb2 receptor.

The antibody can be a polyclonal and/or monoclonal, as such methods for making polyclonal and/or monoclonal antibodies or hybridomas secreting such monoclonal antibodies are well known in the art and are as described above. In certain other embodiments, the antibody specifically recognizes a difference in post-translational modification of the Erbb2Δ16 receptor, the Erbb2Δ16 protein, Erbb2Δ16 domain, or agonist thereof as compared to the wild type Erbb2 receptor. For example, in one embodiment, the antibody specifically binds an Erbb2Δ16 receptor, or to a specific Erbb2Δ16 protein, Erbb2Δ16 domain, or agonist thereof.

In another embodiment of the invention, an antibody is made directed to an Erbb2 domain, or to an ERBB2Δ16 domain, whereby the domain consists of an amino acid sequence having at least 75% amino acid sequence identity to AGATLERPKTLSPGK (SEQ ID NO:4); or having at least 75% amino acid sequence identity to AGATLERAKTLSPGK (SEQ ID NO:5). An antibody also can be made directed to an Erbb2 domain, or to an ERBB2Δ16 domain, whereby the domain consists of an amino acid sequence having at least 80%, at least 85%, at least 90%, or at least 95% amino acid sequence identity to AGATLERPKTLSPGK (SEQ ID NO:4).; or having at least 80%, at least 85%, at least 90%, or at least 95% amino acid sequence identity to AGATLERAKTLSPGK (SEQ ID NO:5).

In certain embodiments, the antibody is a murine monoclonal antibody. In other embodiments, the antibody may comprise murine antigen binding region residues and human antibody residues. In a preferred embodiment, the antibody down-regulates signaling through the Erbb2Δ16 receptor. The present invention also includes immunotoxins which are conjugates of a cytotoxic moiety and the antibodies provided herein. The present invention further includes hybridomas producing the monoclonal antibodies described herein.

The present invention further provides methods of detecting the presence of a tumor in a subject comprising, providing a biological sample; and determining the presence of a detectable amount of an Erbb2 variant in the biological sample from the subject, wherein the presence of an increased level of the Erbb2 variant in the biological sample as compared to a normal control indicates the presence of a tumor correlated with the presence of an Erbb2 variant. In certain embodiments, the methods utilize a polyclonal or monoclonal antibody which specifically binds to an Erbb2 variant that has a mutation in the region of Exon 15 to Exon 17 of Erbb2 or to an Erbb2 isoform that differs in its glycosylation profile from a wild type Erbb2 isoform. Such antibodies are described herein.

The present invention provides that ES cells are a unique way to model CSCs, because ES cells can be grown on a large scale in defined media, and the transforming events discussed herein are observed very early. One embodiment of the present invention, therefore, provides compositions of cancer stem cells and media for culturing the same. The present invention relates to modified defined culture compositions comprising a basal salt nutrient solution, bFGF, IGF-I, and Activin A, wherein the composition is essentially serum free and wherein the composition does not comprise heregulin. In certain embodiments, the composition further comprises transferrin, and a serum albumin selected from the group consisting of bovine serum albumin and human serum albumin.

The present invention further includes cell compositions comprising a mammalian and/or human embryonic stem cell proliferating on an extracellular matrix in the presence of a defined medium, wherein the cell composition is essentially free of feeder cells and essentially serum free, and wherein the defined medium comprises a basal salt nutrient solution, bFGF, IGF-I, and Activin A, and wherein the composition does not comprise heregulin. In one embodiment, the cell composition further comprises transferrin, and a serum albumin selected from the group consisting of bovine serum albumin and human serum albumin. The present invention contemplates that in certain embodiments the mammalian and/or human embryonic stem cell is selected from the group consisting of an embryonic stem cell, an ICM/epiblast cell, a primitive ectoderm cell, a primordial germ cell, a teratocarcinoma cell, a tissue specific stem cell, and a cancer stem cell. The present invention also includes methods of culturing a mammalian and/or human embryonic stem cell comprising providing a mammalian and/or human embryonic stem cell; plating the cell on an extracellular matrix; and contacting the cell with a defined medium that is essentially serum free comprising a basal salt nutrient solution, bFGF, IGF-I, and Activin A, and wherein the medium does not comprise heregulin.

The present invention also provides methods of producing an embryonic stem cell culture that is capable of being stably maintained in a modified defined culture medium comprising the steps of: a) introducing into an embryonic stem cell a vector comprising a nucleic acid that encodes an Erbb2 receptor that has a mutation in the region of Exon 15 to Exon 17 of the Erbb2 receptor; and b) growing the embryonic stem cells in a modified defined culture medium; wherein the modified defined culture medium comprises a basal salt nutrient solution, bFGF, IGF-I, and Activin A, and wherein the composition is essentially serum free and wherein the composition does not comprise heregulin. In a preferred embodiment, the Erbb2 receptor is Erbb2Δ16.

BRIEF DESCRIPTION OF THE DRAWINGS

FIG. 1 shows a known Erbb2 isoform (Isoform a, or "Erbb2a"; SEQ ID NO:1). The Erbb2 Isoform b comes from a 5' splice variant where an internal methionine residue is used to initiate translation. The N-terminal sequence shown in italics (30 residues) is not present in Isoform b. A predicted transmembrane region is shown in grey with a double underline. Exon 16 is shown in bold with an underline. Cysteines are in lowercase and bold. Potential sites for N-linked glycosylation (N-x-S/T) are shown in bold italics with an underline.

FIGS. 2A, 2B, and 2C are graphs showing that both normal (BG01, BG02 and BG03) and variant (BG01v, BG01vDC and BG02DC) hESCs expressed wild type Erbb2 mRNA and Erbb2Δ16 mRNA. The cells were cultured under parental or defined culture (DC) conditions. Quantitative PCR was performed on cDNA isolated from the hESCs using previously described primer sequences (Castiglioni et al., 2006, Endocr. Relat. Cancer, 13(1):221-32), and the relative expression levels were determined by the ΔΔCT method. Panels A and B show the relative expression levels of wild type Erbb2 mRNA and Erbb2Δ16 mRNA, respectively. Panel C shows the expression ratio of Erbb2 mRNA and Erbb2Δ16 mRNA.

FIG. 6 is a cDNA nucleotide sequence of Erbb2Δ16 (SEQ ID NO:2). The bolded nucleotides depict the coding regions of the gene.

FIG. 7 is a deduced amino acid sequence of the Erbh2Δ16 nucleotide sequence described in FIG. 6 (SEQ ID NO:3).

FIG. 8 is an amino acid sequence alignment between the Erbb2 isoform as described in FIG. 1 (SEQ ID NO:1) and the deduced amino acid sequence of the Erbb2Δ16 nucleotide sequence as described in FIG. 7 (SEQ ID NO:3). The two sequences share about 98% amino acid sequence identity. The 16 amino acids found in the Erbb2a sequence ("Erbb2a"; SEQ ID NO:1) but not in the Erbb2Δ16 amino acid sequence ("D16"; SEQ ID NO:3) is in bold and italicized. Also, there is an amino acid change at position 1155 whereby the D16 sequence contains an Alanine (A) while the Erbb2a sequence contains a Proline (P); bolded and double-underlined.

FIG. 9 shows phosphorylation levels of Erbb2 and Erbb3 in hESCs. (A) BG01 and BG01v cells were grown in defined condition-heregulin/Activin A/IGF-1/FGF (DC-HAIF) media. The hESCs were starved of growth factors overnight ("Starved"), or starved then pulsed with 10 ng/ml Heregulin ("HRG pulse"). Cell lysates were prepared and examined for phosphorylation of Erbb2 and Erbb3 by RTK blotting. (B) The spots were quantified, normalized against controls, and charted as normalized relative intensity. BG01 cells exhibited relatively even phosphorylation of Erbb2 and Erbb3 in steady state conditions, whereas BG01v cells exhibited hypophosphorylation of Erbb2 and hyperphosphorylation of Erbb3. While at a lower overall intensity, a similar pattern was also observed in the starved conditions. Both cell lines responded to acute HRG stimulation with strong phosphorylation of both ERBB2 and 3.

DETAILED DESCRIPTION OF THE INVENTION

Figure 3:
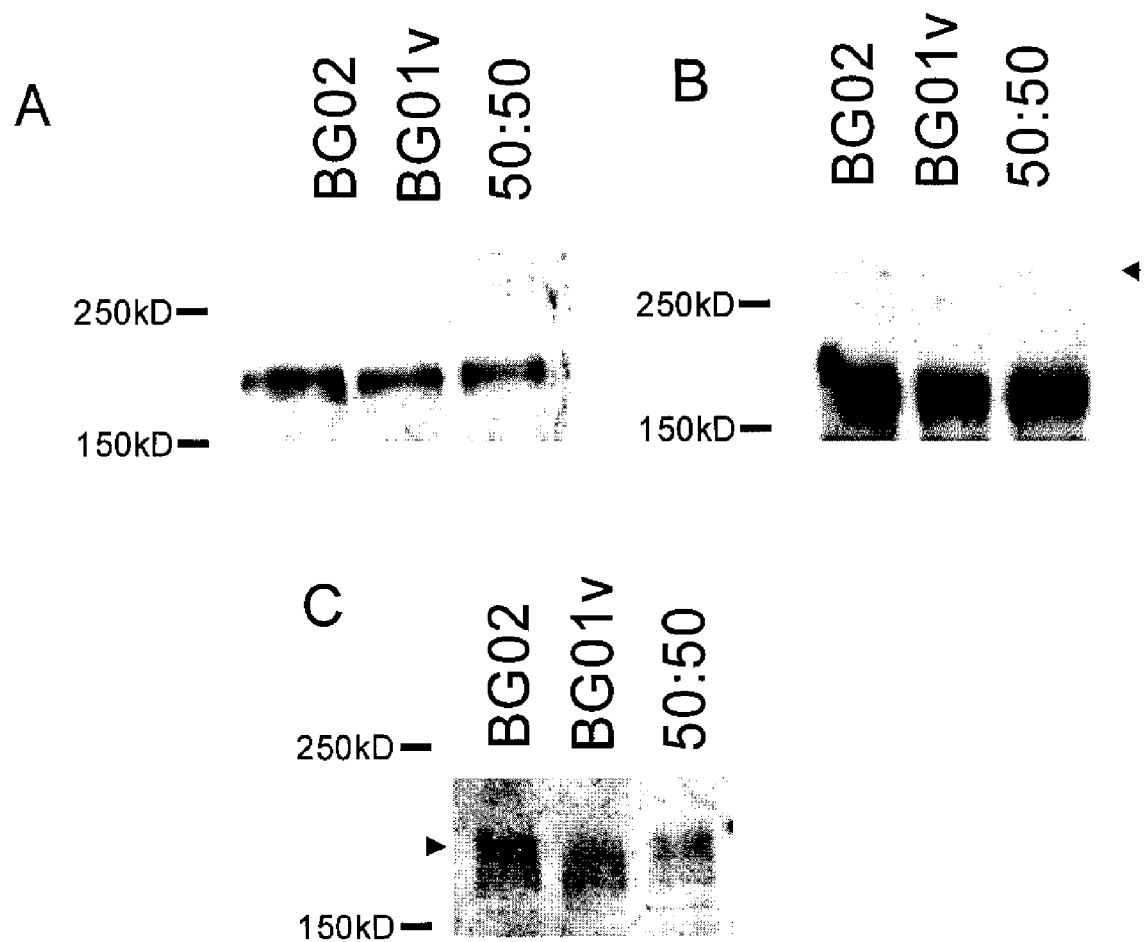
FIGS. 3A, 3B, and 3C show the results of Western blotting of Erbb2 in hESCs. BG02 and BG01v cells were grown in defined conditions containing NRG, LR-IGF1, FGF2 and Activin A. Protein lysates were separated by 6% PAGE under reducing (Panel A) and non-reducing (Panel B) conditions. 30 ug of BG02 and BG01v lysates were loaded separately, and a 50:50 mix of these samples (15 ug each) were run in the third lane. The blots were probed with an anti-Erbb2 antibody. Panel C shows the same samples as in Panel A, however, the samples were run further to increase the separation of large molecules. Probing the blot with the same anti-Erbb2 antibody revealed migration differences between normal BG02 and BG01v cells.

The present invention provides that ES cells and variant ES cells may be used to model very early transformation events that happen to tissue stem cells (i.e. changes to hChr17 and Erbb2). As disclosed herein, BG01v cells, which can grow independently of heregulin, are a good model to study these early transformation events.

The present invention provides methods of treating a patient having a tumor that expresses a transforming isoform of the Erbb2 receptor in rare tumor CSCs, comprising administering to said patient an antibody in an amount effective to eliminate or reduce the patient's tumor, wherein the antibody binds specifically to an Erbb2 receptor that has a mutation in the region of Exon 15 to Exon 17 of Erbb2 or to an Erbb2 isoform that differs in its glycosylation profile from a wild type Erbb2 isoform. In certain embodiments, the antibody binds specifically to an Erbb2Δ16 receptor. The invention contemplates that in certain embodiments, the antibody specifically recognizes a difference in post-translational modification of the Erbb2Δ16 receptor as compared to the wild type Erbb2 receptor. In preferred embodiments, the antibody inhibits signaling through the Erbb2Δ16 receptor.

In certain embodiments, the antibody is conjugated to a cytotoxic moiety such as a radioactive isotope or toxin (See Lambert, 2005, Curr. Opin. Pharm., 5:543-549 for a review of conjugates). It is contemplated that in certain embodiments, the antibody activates complement or mediates antibody dependent cellular cytotoxicity. In certain embodiments, the antibody is a monoclonal antibody. In some embodiments, the carcinoma is selected from the group consisting of renal carcinoma, human breast carcinoma, gastric carcinoma, and salivary gland carcinoma. The invention contemplates that in some embodiments, the methods may involve administering a therapeutically effective amount of a liposome comprising said antibody. The liposome may be coated with the antibody and may be filled with a cytotoxic compound. The present invention provides that in certain embodiments, the antibody is capable of activating complement in the patient or capable of mediating antibody dependent cellular cytotoxicity in the patient. The present invention also includes immunotoxins which are conjugates of a cytotoxic moiety and the antibodies provided herein.

The present invention also provides a monoclonal antibody which specifically binds to an Erbb2 receptor that has a mutation in the region of Exon 15 to Exon 17 of Erbb2, or to an Erbb2 isoform that differs in its glycosylation profile from a wild type Erbb2 isoform, and which inhibits growth of tumor stem cells which express the Erbb2 receptor isoform in a patient treated with an effective amount of said antibody. In a preferred embodiment, the antibody specifically binds an Erbb2Δ16 receptor. In certain embodiments, the antibody specifically recognizes a difference in post-translational modification of an Erbb2 variant isoform as compared to the wild type Erbb2 isoform. The present invention further includes hybridomas producing the monoclonal antibodies described herein.

The present invention further provides methods of detecting the presence of a tumor in a subject comprising, providing a biological sample; and determining the presence of a detectable amount of an Erbb2 variant in the biological sample from the subject, wherein the presence of an increased level of the Erbb2 variant in the biological sample as compared to a normal control indicates the presence of a tumor correlated with the presence of an Erbb2 variant. Also contemplated are methods of determining the prognosis of a patient with a tumor comprising, providing a biological sample from the patient; and determining the presence of a detectable amount of an Erbb2 variant isoform in the biological sample from the subject; wherein the presence of an increased level of the Erbb2 variant isoform in the biological sample as compared to the level in a normal control indicates a decreased chance of long term survival. In certain embodiments, the methods utilize a monoclonal antibody which specifically binds to an Erbb2 variant that has a mutation in the region of Exon 15 to Exon 17 of Erbb2 or to an Erbb2 isoform that differs in its glycosylation profile from a wild type Erbb2 isoform. In one embodiment, the antibody specifically binds an Erbb2Δ16 receptor. In certain other embodiments, the antibody specifically recognizes a difference in post-translational modification of the Erbb2Δ16 receptor as compared to the wild type Erbb2 receptor.

One embodiment of the present invention relates to a medium for culturing cells, comprising a basal salt nutrient solution, bFGF, IGF-I, and Activin A, wherein the composition is essentially serum free and wherein the composition does not comprise heregulin.

Also encompassed within the bounds of the invention are cell compositions comprising a mammalian embryonic stem cell proliferating on an extracellular matrix in the presence of a defined medium, wherein the cell composition is essentially free of feeder cells and essentially serum free, and wherein the defined medium comprises a basal salt nutrient solution, bFGF, IGF-I, and Activin A, and wherein the composition does not comprise heregulin.

Additionally, the invention is directed to a method of culturing mammalian embryonic stem cells comprising a) providing a mammalian embryonic stem cell; b) plating the cell on an extracellular matrix; and c) contacting the cell with a defined medium that is essentially serum free comprising a basal salt nutrient solution, bFGF, IGF-I, and Activin A, and wherein the medium does not comprise heregulin. In one embodiment of the foregoing, the contact with the defined medium is in the absence of a feeder layer. In a further embodiment, the mammalian embryonic stem cell is cultured on feeder cells prior to plating on the extracellular matrix. In another embodiment, the extracellular matrix is matrigel.

In certain embodiments of the present invention, the pluripotent mammalian embryonic stem cell is selected from the group consisting of an embryonic stem cell, an ICM/epiblast cell, a primitive ectoderm cell, a primordial germ cell, a teratocarcinoma cell, or a cancer stem cell. In one embodiment, the mammalian embryonic stem cell is a human embryonic stem cell.

The present invention also provides methods of producing an embryonic stem cell culture that is capable of being stably maintained in a modified defined culture medium comprising the steps of: a) introducing into an embryonic stem cell a vector comprising a nucleic acid that encodes an Erbb2 receptor that has a mutation in the region of Exon 15 to Exon 17 of the Erbb2 receptor; and b) growing the embryonic stem cells in a modified defined culture medium; wherein the modified defined culture medium comprises a basal salt nutrient solution, bFGF, IGF-I, and Activin A, and wherein the composition is essentially serum free and wherein the composition does not comprise heregulin. In a preferred embodiment, the Erbb2 receptor is Erbb2Δ16.

Unless otherwise noted, the terms used herein are to be understood according to conventional usage by those of ordinary skill in the relevant art. In addition to the definitions of terms provided below, definitions of common terms in molecular biology may also be found in Rieger et al, 1991 Glossary of genetics: classical and molecular, 5th Ed., Berlin: Springer-Verlag; and in Current Protocols in Molecular Biology, F. M. Ausubel et at, Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et at, 1989 Molecular Cloning, Second Edition, Cold Spring Harbor Laboratory, Plainview, N.Y.; Maniatis et at., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

Human pluripotent cells offer unique opportunities for investigating early stages of human development as well as for therapeutic intervention in several disease states, such as diabetes mellitus and Parkinson's disease. For example, the use of insulin-producing β-cells derived from hESCs would offer a vast improvement over current cell therapy procedures that utilize cells from donor pancreases. Currently cell therapy treatments for diabetes mellitus, which utilize cells from donor pancreases, are limited by the scarcity of high quality islet cells needed for transplant. Cell therapy for a single Type I diabetic patient requires a transplant of approximately $8 \times 10^8$ pancreatic islet cells (Shapiro et al., 2000, N Engl J Med 343:230-238; Shapiro et al., 2001a, Best Pract Res Clin Endocrinol Metab 15:241-264; Shapiro et al., 2001b, Bmj 322:861). As such, at least two healthy donor organs are required for to obtain sufficient islet cells for a successful transplant. HESCs offer a source of starting material from which to develop substantial quantities of high quality differentiated cells for human cell therapies. Importantly, such cells must be obtained and/or cultured in conditions that are compatible with the expected regulatory guidelines governing clinical safety and efficacy. Such guidelines likely will require the use of a chemically defined media. The development of such chemically defined/GMP standard conditions is necessary to facilitate the use of hESCs and cells derived from hESCs for therapeutic purposes in humans.

As used herein, a basal salt nutrient solution refers to a mixture of salts that provide cells with water and certain bulk inorganic ions essential for normal cell metabolism, maintain intra- and extra-cellular osmotic balance, provide a carbohydrate as an energy source, and provide a buffering system to maintain the medium within the physiological pH range. Non-limiting examples of basal salt nutrient solutions include Dulbecco's Modified Eagle's Medium (DMEM), Minimal Essential Medium (MEM), Basal Medium Eagle (BME), RPM1 1640, Ham's F-10, Ham's F-12, α-Minimal Essential Medium (αMEM), Glasgow's Minimal Essential Medium (G-MEM), and Iscove's Modified Dulbecco's Medium, and mixtures thereof. In one embodiment, the basal salt nutrient solution is an approximately 50:50 mixture of DMEM and Ham's F12.

As used herein, "Erbb2/3 ligand" refers to a ligand that binds to and activates an Erbb2/Erbb3 heterodimeric receptor, inducing downstream signaling of this pathway. Typically, the ligand activates the Erbb2/Erbb3 receptor by first binding to Erbb3 which then dimerizes with Erbb2. Non-limiting examples of Erbb2/3 ligands include Neuregulin-1; splice variants and isoforms of Neuregulin-1, including but not limited to HRG-β, HRG-α, Neu Differentiation Factor (NDF), Acetylcholine Receptor-Inducing Activity (ARIA), Glial Growth Factor 2 (GGF2), and Sensory And Motor Neuron-Derived Factor (SMDF); Neuregulin-2; splice variants and isoforms of Neuregulin-2, including but not limited to NRG2-β; Epiregulin; and Biregulin.

As used herein, the term "member of the TGF-β family" refers to growth factors that are generally characterized by one of skill in the art as belonging to the TGF-β family, either due to homology with known members of the TGF-β family, or due to similarity in function with known members of the TGF-β family. In certain embodiments, the member of the TGF-β family is selected from the group consisting of Nodal, Activin A, Activin B, TGF-β, BMP2 and BMP4. In one embodiment, the member of the TGF-β family is Activin A.

As used herein, the term "activator of an FGF receptor" refers to growth factors that are generally characterized by one of skill in the art as belonging to the FGF family, either due to homology with known members of the FGF family, or due to similarity in function with known members of the FGF family. In certain embodiments, the activator of an FGF receptor is an FGF, such as, but not limited to bFGF (FGF2) and α-FGF.

As used herein, "essentially free" means that a de minimus or reduced amount of a component, such as but not limited to heregulin, may be present that does not eliminate the improved bioactive culturing capacity of the medium or environment. For example, a medium essentially free of heregulin can contain less than 10, 9, 8, 7, 6, 5, 4, 3, 2, or 1 ng/ml of heregulin, wherein the presently improved bioactive maintenance capacity of the medium or environment is still observed. In certain embodiments of the present invention, the medium that is essentially free of heregulin does not contain exogenously added heregulin, or only contains trace amounts of heregulin as are present from the isolation of other components that are added to the defined media.

As used herein, the term "activator of IGF-1R" refers to mitogens that play a pivotal role in regulating cell proliferation, differentiation, and apoptosis. The effects of an activator of IGF-1R are typically mediated through IGF-1R, although they can be mediated through other receptors. The IGF-1R is also involved in cell transformation induced by tumor virus proteins and oncogene products, and the interaction is regulated by a group of specific binding proteins (IGFBPs). In addition, a large group of IGFBP proteases hydrolyze IGFBPs, resulting in the release of bound IGFs that then resume their ability to interact with IGF-1R. For the purpose of this invention, the ligands, the receptors, the binding proteins, and the proteases are all considered to be activators of IGF-1R. In one embodiment, the activator of IGF-1R is insulin. In one embodiment, the activator of IGF-1R is IGF-1, or IGF-2. In a further embodiment, the IGF-1 is an IGF-1 analog. Non-limiting examples of IGF-1 analogs include LongR$^3$IGF-1, Des(1-3)IGF-1, [Arg$^3$]IGF-1, [Ala$^{31}$]IFG-1, Des(2,3)[Ala$^{31}$]IGF-1, [Leu$^{24}$]IGF1, Des(2,3)[Leu$^{24}$]IGF-1, [Leu$^{60}$]IGF-1, [Ala$^{31}$][Leu$^{60}$]IGF-1, [Leu$^{24}$][Ala$^{31}$]IGF-1, and combinations thereof. In a further embodiment, the IFG-1 analog is LongR$^3$IGF-1, a recombinant analog of human insulin growth factor-1 (JRH Biosciences; Yandell et al., 2004 BioProcess Intl., 56-64). LongR$^3$IGF-1 has greatly decreased affinity for IGFBPs, and may therefore be more bioactive in cell culture.

As used herein, the term "variant" or "mutein" or "modified" polypeptide or protein and their equivalents, includes chimeric or fusion polypeptides, homologs, analogs, orthologs, and paralogs. The invention also provides chimeric or fusion polypeptides. As used herein, a "chimeric polypeptide" or "fusion polypeptide" comprises at least a portion of a member of the reference polypeptide operatively linked to a second, different polypeptide. The second polypeptide has an amino acid sequence corresponding to a polypeptide which is not substantially identical to the reference polypeptide, and which is derived from the same or a different organism. With respect to the fusion polypeptide, the term "operatively linked" is intended to indicate that the reference polypeptide and the second polypeptide are fused to each other so that both sequences fulfill the proposed function attributed to the sequence used. The second polypeptide can be fused to the N-terminus or C-terminus of the reference polypeptide. For example, in one embodiment, the fusion polypeptide is a GST-IGF-1 fusion polypeptide in which an IGF-1 sequence is fused to the C-terminus of the GST sequences. Such fusion polypeptides can facilitate the purification of recombinant polypeptides. In another embodiment, the fusion polypeptide can contain a heterologous signal sequence at its N-terminus. In certain host cells (e.g., mammalian host cells), expression and/or secretion of a polypeptide can be increased through use of a heterologous signal sequence.

In yet another embodiment of the invention, there is provided protein variants including mutations such as substitutions, additions, deletions, or any combination thereof, and are typically produced by site-directed mutagenesis using one or more mutagenic oligonucleotide(s) according to methods described herein, as well as according to methods known in the art (see, for example, Sambrook et al., MOLECULAR CLONING: A LABORATORY MANUAL, 3rd Ed., 2001, Cold Spring Harbor, N.Y. and Berger and Kimmel, METHODS IN ENZYMOLOGY, Volume 152, Guide to Molecular Cloning Techniques, 1987, Academic Press, Inc., San Diego, Calif., which are incorporated herein by reference).

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts).

In preferred embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in PROTEINS, STRUCTURES AND MOLECULAR PRINCIPLES, (Creighton, Ed.), 1984, W.H. Freeman and Company, New York; INTRODUCTION TO PROTEIN STRUCTURE (C. Branden and J. Tooze, eds.), 1991, Garland Publishing, New York, N.Y.; and Thornton et al., 1991, Nature 354:105, each of which are incorporated herein by reference.

Peptide analogs are commonly used in the pharmaceutical industry as non-peptide drugs with properties analogous to those of the template peptide. These types of non-peptide compound are termed "peptide mimetics" or "peptidomimetics". See Fauchere, 1986, *Adv. Drug Res.* 15:29; Veber & Freidinger, 1985, *TINS* p. 392; and Evans et al., 1987, *J. Med. Chem.* 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as a human antibody, but have one or more peptide linkages optionally replaced by a linkage selected from: —CH2-NH—, —CH2-S—, —CH2-CH2-, —CH=CH-(cis and trans), —COCH2-, —CH(OH)CH2-, and —CH2SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference for any purpose); for example, by adding internal cysteine residues capable of forming intramolecular disulfide bridges which cyclize the peptide.

The Erbb2 variant and agonists and antagonists thereof as described herein include those polypeptides and functional fragments thereof with additional amino acid substitutions, including those substitutions which enable the site-specific coupling of at least one non-protein polymer, such as polypropylene glycol, polyoxyalkylene, or polyethylene glycol (PEG) molecule to the mutein. Site-specific coupling of PEG, for example, allows the generation of a variant which possesses the benefits of a polyethylene-glycosylated (PEGylated) molecule, namely increased plasma half life and decreased immunogenicity while maintaining greater potency over non-specific PEGylation strategies such as N-terminal and lysine side-chain PEGylation. Methods providing for efficient PEGylation are described in U.S. application Ser. No. 10/820,559, which is incorporated herein by reference in its entirety.

In certain embodiments, protein variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

Additional preferred variants include cysteine variants wherein one or more cysteine residues are deleted from or substituted for another amino acid (e.g., serine) compared to the parent amino acid sequence. Cysteine variants may be useful when proteins must be refolded into a biologically active conformation such as after the isolation of insoluble inclusion bodies. Cysteine variants generally have fewer cysteine residues than the native protein, and typically have an even number to minimize interactions resulting from unpaired cysteines.

The above polypeptide variants are illustrative of the types Erbb2 variants and agonists and antagonists thereof to be used in the methods claimed herein, but are not exhaustive of the types of variations of the claimed invention which may be embodied by the invention, Derivatives of the above polypeptide which fit the criteria of the claims should also be considered. All of the polypeptides and functional fragments thereof can be screened for efficacy following the methods taught herein and in the examples.

Also inherent in this invention is the selection of the specific site of amino acid substitution which enables proper folding of the polypeptide following expression. The Erbb2 variant and agonists and antagonists thereof bind to their receptors with an affinity loss not greater than 10-fold relative to that of the wild type isoform or Erbb2.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary and tertiary protein structures. See Moult, 1996, Curr. Op. in Biotech. 7:422-427; Chou et al., 1974, Biochemistry 13:222-245; Chou et al., 1974, Biochemistry 113:211-222; Chou et al., 1978, Adv. Enzymol Reat. Areas Mol. Biol. 47.45-148; Chou et al., 1979, Ann. Rev. Biochem. 47:251-276; and Chou et al., 1979, Biophys. J. 26:367-384; Monge, A. et al., PNAS USA, 1994, 91:5027-5029; Monge, A. et al., J. Mol. Biol., 1995, 247: 995-1012; Levitt, J. Mol. Biol. 170, 723 (1983); Hinds and Levitt, J. Mol. Biol. 243, 668 (1994); Ortiz et al., Proc. Natl. Acad. Sci. USA 95, 1020 (1998a); Skolnick et al., J. Mol. Biol. 265, 217 (1997); Simons et al., Proteins 34, 82 (1999a); Shortle et al., Proc. Natl. Acad. Sci. USA 95, 11158 (1998); Sun et al., Protein Engineering 8, 769 (1995); Monge et al., Proc. Natl. Acad. Sci. USA 91, 5027 (1994); Monge et al., J. Mol. Biology. 247, 995 (1995); M. Standley et al., J Mol Bio 285, 1691 (1999); Scheraga et al., 3 Global Optimization 15, 235 (1999); Liwo et al., Proc. Natl. Acad. Sci. USA 96, 5482 (1999); Lee et al., Biopolymers 46, 103 (1998); Srinivasan and Rose, PNAS 96, 14258 (1999); Yue and Dill, Protein Science 5, 254 (1996); Dill et al., J. Computational Biology 4, 227 (1997); Orengo et al., Proteins Suppl. 3, 149 (1999); and U.S. Pat. No. 6,832,162, which are all incorporated herein in their entirety by reference.

Additional methods of predicting secondary structure include "threading" (Jones, 1997, Curr. Opin. Struct. Biol. 7:377-87; Sippl et al., 1996, Structure 4:15-19), "profile analysis" (Bowie et al., 1991, Science 253:164-170; Gribskov et al., 1990, Meth. Enzym. 183:146-159; Gribskov et al., 1987, Proc. Nat. Acad. Sci. 84:4355-4358), and "evolutionary linkage" (See Holm, 1999, supra; and Brenner, 1997, supra).

Moreover, computer programs are currently available to assist with predicting secondary and tertiary structure. One method of predicting secondary and/or tertiary structure is based upon homology modeling. For example, two polypeptides or proteins that have a sequence identity of greater than 30%, or similarity greater than 40% often have similar structural topologies. The recent growth of the protein structural database has provided enhanced predictability of secondary and/or tertiary structure, including the potential number of folds within a polypeptide's or protein's structure. See Holm et al., 1999, Nucl. Acid. Res. 27:244-247. It has been suggested (Brenner et al., 1997, Curr. Op. Struct. Biol. 7:369-376) that there are a limited number of folds in a given polypeptide or protein and that once a critical number of structures have been resolved, structural prediction will become dramatically more accurate.

In addition to the proteins and variants described above, the present invention also encompasses protein fragments and fusion polypeptides, the present invention includes homologs and analogs of naturally occurring polypeptides. "Homologs" are defined herein as two nucleic acids or polypeptides that have similar, or "identical," nucleotide or amino acid sequences, respectively. Homologs include allelic variants, orthologs, paralogs, agonists, and antagonists as defined hereafter. The term "homolog" further encompasses nucleic acid molecules that differ from a reference nucleotide sequence due to degeneracy of the genetic code and thus encode the same polypeptide as that encoded by the reference nucleotide sequence. As used herein, "naturally occurring" refers to a nucleic or amino acid sequence that occurs in nature. An agonist of a polypeptide can retain substantially the same, or a subset, of the biological activities of the polypeptide. An antagonist of a polypeptide can inhibit one or more of the activities of the naturally occurring form of the polypeptide.

It is contemplated that the defined medium comprises a basal salt nutrient solution, bFGF, IGF-I, and Activin A, and wherein the composition is essentially serum free and wherein the composition does not comprise heregulin. In addition, other components such as serum albumin, transferrin, L-glutamine, non-essential amino acids, amino acids, lipids, ascorbic acid, trace elements, antibiotics, β-Mercaptoethanol, and similar components may be present. Serum albumin is preferably selected from the group consisting of bovine serum albumin and human serum albumin.

It is understood that at different points during culturing the pluripotent cells, various components may be added to the cell culture such that the medium can contain components other than those described herein. However, it is contemplated that at least at one point during the preparation of the culture, or during the culture of the pluripotent cells, the modified defined medium can comprise a basal salt nutrient solution, bFGF, IGF-I, and Activin A, and wherein the composition is essentially serum free and wherein the composition does not comprise heregulin.

In particular embodiments of the invention, if the member of the TGF-β family is present, it activates SMAD 2 or 3. In certain embodiments, the member of the TGF-β family is selected from the group consisting of Nodal, Activin A, Activin B, TGF-β, and BMP2. In a further embodiment, the member of the TGF-β family is Activin A. It is contemplated that if used, Activin A is initially present at a concentration of approximately 0.01 ng/ml to approximately 1000 ng/ml, more preferably approximately 0.1 ng/ml to approximately 100 ng/ml, more preferably approximately 0.1 ng/ml to approximately 25 ng/ml, or most preferably at a concentration of approximately 10 ng/ml.

It is contemplated that if an activator of IGF-1R is present, it is selected from the group consisting of insulin and an insulin-like growth factor. In one embodiment, the insulin like growth factor is IGF-1 or IGF-2. In one embodiment, the insulin-like growth factor is IGF-1, which can be LongR$^3$IGF-1. It is contemplated that LongR$^3$IGF-1 is initially present at a concentration of approximately 1 ng/ml to approximately 1000 ng/ml, more preferably approximately 5 ng/ml to approximately 500 ng/ml, more preferably approximately 50 ng/ml to approximately 500 ng/ml, more preferably approximately 100 ng/ml to approximately 300 ng/ml, or at a concentration of approximately 100 ng/ml.

In one embodiment, the activator of an FGF receptor is FGF2. It is contemplated that if FGF2 is present, it is initially present at a concentration of approximately 0.1 ng/ml to approximately 100 ng/ml, more preferably approximately 0.5 ng/ml to approximately 50 ng/ml, more preferably approximately 1 ng/ml to approximately 25 ng/ml, more preferably approximately 1 ng/ml to approximately 12 ng/ml, or most preferably at a concentration of approximately 8 ng/ml.

In a particular an embodiment of the invention, the serum albumin is selected from bovine serum albumin and human serum albumin. It is contemplated that the serum albumin is initially present at a concentration of from approximately 0.02-5.0%, from approximately 0.05-2% or from approximately 0.1-0.5%.

It is contemplated that the composition can further comprise trace elements. Trace elements can be purchased commercially, for example, from Mediatech. Non-limiting examples of trace elements include $AlCl_3$, $AgNO_3$, $Ba(C_2H_3O_2)_2$, $CdCl_2$, $CdSO_4$, $CoCl_2$, $CrCl_3$, $Cr_2(SO_4)_3$, $CuSO_4$, ferric citrate, $GeO_2$, KI, KBr, LI, molybdic acid, $MnSO_4$, $MnCl_2$, NaF, $Na_2SiO_3$, $NaVO_3$, $NH_4VO_3$, $(NH_4)_6Mo_7O_{24}$, $NiSO_4$, RbCl, selenium, $Na_2SeO_3$, $H_2SeO_3$, selenite.2Na, selenomethionone, $SnCl_2$, $ZnSO_4$, $ZrOCl_2$, and mixtures and salts thereof. If selenium, selenite or selenomethionone is present, it is at a concentration of approximately 0.002 to approximately 0.02 mg/L.

It is contemplated that amino acids can be added to the defined media. Non-limiting examples of such amino acids are Glycine, L-Alanine, L-Alanyl-L-Glutamine, L-Glutamine/Glutamax, L-Arginine hydrochloride, L-Asparagine-$H_2O$, L-Aspartic acid, L-Cysteine hydrochloride-$H_2O$, L-Cystine 2HCl, L-Glutamic Acid, L-Histidine hydrochloride-$H_2O$, L-Isoleucine, L-Leucine, L-Lysine hydrochloride, L-Methionine, L-Phenylalanine, L-Proline, L-Hydroxyproline, L-Serine, L-Threonine, L-Tryptophan, L-Tyrosine disodium salt dihydrate, and L-Valine. In certain embodiments, the amino acid is L-Isoleucine, L-Phenylalanine, L-Proline, L-Hydroxyproline, L-Valine, and mixtures thereof.

It is also contemplated that the defined medium can comprise ascorbic acid. Preferably ascorbic acid is present at an initial concentration of approximately 1 mg/L to approximately 1000 mg/L, or from approximately 2 mg/L to approximately 500 mg/L, or from approximately 5 mg/L to approximately 100 mg/L, or from approximately 10 mg/L to approximately 100 mg/L or approximately at 50 mg/L.

In certain embodiments, the defined medium composition comprises an inactivator of BMP signaling. As used herein, an "inactivator of BMP signaling" refers to an agent that antagonizes the activity of one or more BMP proteins or any of their upstream or downstream signaling components through any of its possible signaling pathways. The compound used to inactivate BMP signaling can be any compound known in the art, or later discovered. Non-limiting examples of inactivators of BMP signaling include dominant-negative, trancated BMP receptor, soluble BMP receptors, BMP receptor-Fc chimeras, noggin, follistatin, chordin, gremlin, cerberus/DAN family proteins, ventropin, high dose activin, and amnionless In certain embodiments, the defined medium can comprise a growth hormone. It is currently contemplated that in certain embodiments, the growth hormone present in the defined medium will be of the same species as the pluripotent mammalian cell that is cultured with the defined media. Thus, for example, if a human cell is cultured, the growth hormone is human growth hormone. The use of growth hormone that is from a species different than the cultured cells is also contemplated. Preferably growth hormone is present at an initial concentration of approximately 0.001 ng/ml to approximately 1000 ng/ml, more preferably approximately 0.001 ng/ml to approximately 250 ng/ml, or more preferably approximately 0.01 ng/ml to approximately 150 ng/ml.

It is preferred that the defined media of the invention is essentially free of serum and serum replacement, and is essentially serum free. As used herein, "essentially serum free" refers to a medium that does not contain serum or serum replacement, or that contains essentially no serum or serum replacement. As used herein, "essentially" means that a de minimus or reduced amount of a component, such as serum or serum replacement, may be present that does not eliminate the improved bioactive culturing capacity of the medium or environment. For example, essentially serum free medium or environment can contain less than 10, 9, 8, 7, 6, 5, 4, 3, 2, or 1% serum wherein the presently improved bioactive maintenance capacity of the medium or environment is still observed. In preferred embodiments of the present invention, the essentially serum free medium does not contain serum or serum replacement, or only contains trace amounts of serum or serum replacement from the isolation of components of the serum or serum replacement that are added to the defined media.

As used herein when referring to a cell, cell line, cell culture, or population of cells, the term "isolated" refers to being substantially separated from the natural source of the cells such that the cell line, cell culture, or population of cells are capable of being cultured in vitro. In addition, the term "isolating" is used to refer to the physical selection of one or more cells out of a group of two or more cells, wherein the cells are selected based on cell morphology and/or the expression of various markers.

As used herein, the term "express" refers to the transcription of a polynucleotide or translation of a polypeptide in a cell, such that levels of the molecule are measurably higher in a cell that expresses the molecule than they are in a cell that does not express the molecule. Methods to measure the expression of a molecule are well known to those of ordinary skill in the art, and include without limitation, Northern blotting, RT-PCT, in situ hybridization, Western blotting, and immunostaining.

As used herein, the term "contacting" (i.e., contacting a cell e.g. a pluripotent cell, with a compound) is intended to include incubating the compound and the cell together in vitro (e.g., adding the compound to cells in culture). The term "contacting" is not intended to include the in vivo exposure of cells to a defined cell medium that may occur naturally in a subject (i.e., exposure that may occur as a result of a natural physiological process). The step of contacting the cell with a defined cell medium comprising a basal salt nutrient solution, bFGF, IGF-I, and Activin A, and wherein the composition is essentially serum free and wherein the composition does not comprise heregulin, can be conducted in any suitable manner. For example, the cells may be treated in adherent culture, or in suspension culture. It is understood that the cells contacted with the defined medium can be further treated with a cell differentiation environment to stabilize the cells, or to differentiate the cells.

The compositions and methods described herein have several useful features. For example, the compositions and methods described herein are useful for modeling the early stages of tumorigenesis. Furthermore, the compositions and methods described herein can also serve for therapeutic intervention in disease states.

As used herein, the term "differentiate" refers to the production of a cell type that is more differentiated than the cell type from which it is derived. The term therefore encompasses cell types that are partially and terminally differentiated.

In certain embodiments of the present invention, the term "enriched" refers to a cell culture that contains more than approximately 50%, 55%, 60%, 65%, 70%, 75%, 80%, 85%, 90%, or 95% of the desired cell lineage.

As used herein, the term "pluripotent human cell" encompasses pluripotent cells obtained from human embryos, fetuses or adult tissues. In one preferred embodiment, the pluripotent human cell is a human pluripotent embryonic stem cell. In another embodiment the pluripotent human cell is a human pluripotent fetal stem cell, such as a primordial germ cell. In another embodiment the pluripotent human cell is a human pluripotent adult stem cell. As used herein, the term "pluripotent" refers to a cell capable of at least developing into one of ectodermal, endodermal and mesodermal cells. As used herein the term "pluripotent" refers to cells that are totipotent and multipotent. As used herein, the term "totipotent cell" refers to a cell capable of developing into all lineages of cells. The term "multipotent" refers to a cell that is not terminally differentiated. As also used herein, the term "multipotent" refers to a cell that, without manipulation (i.e., nuclear transfer or dedifferentiation inducement), is incapable of forming differentiated cell types derived from all three germ layers (mesoderm, ectoderm and endoderm), or in other words, is a cell that is partially differentiated. The pluripotent human cell can be selected from the group consisting of a human embryonic stem (ES) cell; a human inner cell mass (ICM)/epiblast cell; a human primitive ectoderm cell, such as an early primitive ectoderm cell (EPL); a human primordial germ (EG) cell; a human teratocarcinoma (EC) cell, a tissue specific stem cell, and a cancer stem cell. As used herein, the term "cancer stem cells" refers to cells that have the capacity to regenerate tumors at high frequency after transplantation and that have the capacity to expand and differentiate to all lineages of the tumor. As used herein, the term "tissue specific stem cells" refers to the progenitor cells of other cells within that tissue.

The human cells of the present invention can be derived using any method known to those of skill in the art. For example, the human pluripotent cells can be produced using de-differentiation and nuclear transfer methods. Additionally, the human ICM/epiblast cell or the primitive ectoderm cell used in the present invention can be derived in vivo or in vitro. EPL cells may be generated in adherent culture or as cell aggregates in suspension culture, as described in WO 99/53021. Furthermore, the human pluripotent cells can be passaged using any method known to those of skill in the art, including, manual passaging methods, and bulk passaging methods such as FACS or other antibody selection and enzymatic or non-enzymatic passaging.

In certain embodiment, the embryonic stem cell has an abnormal karyotype. In one embodiment, a majority of the embryonic stem cells have an abnormal karyotype. It is contemplated that greater than 50%, 55%, 60%, 65%, 70%, 75%, 80%, 85%, 90% or greater than 95% of metaphases examined will display an abnormal karyotype. In certain embodiments, the abnormal karyotype is evident after the cells have been cultured for greater than 5, 6, 7, 8, 9, 10, 11, 12, 13, 14, 15, or 20 passages. In one embodiment, the abnormal karyotype comprises a trisomy of at least one autosomal chromosome, wherein the autosomal chromosome is selected from the group consisting of chromosomes 1, 7, 8, 12, 14, and 17. In another embodiment, the abnormal karyotype comprises a trisomy of more than one autosomal chromosome, wherein at least one of the more than one autosomal chromosomes is selected from the group consisting of chromosomes 1, 7, 8, 12, 14, and 17. In one embodiment, the autosomal chromosome is chromosome 12 or 17. In another embodiment, the abnormal karyotype comprises an additional sex chromosome. In one embodiment, the karyotype comprises two X chromosomes and one Y chromosome. It is also contemplated that translocations of chromosomes may occur, and such translocations are encompassed within the term "abnormal karyotype." Combinations of the foregoing chromosomal abnormalities and other chromosomal abnormalities are also encompassed by the invention.

A cell differentiating medium or environment may be utilized to partially, terminally, or reversibly differentiate the pluripotent cells of the present invention. In accordance with the invention the medium of the cell differentiation environment may contain a variety of components including, for example, KODMEM medium (Knockout Dulbecco's Modified Eagle's Medium), DMEM, Ham's F12 medium, FBS (fetal bovine serum), FGF2 (fibroblast growth factor 2), KSR or HLIF (human leukemia inhibitory factor). The cell differentiation environment can also contain supplements such as L-Glutamine, NEAA (non-essential amino acids), P/S (penicillin/streptomycin), N2 and β-mercaptoethanol (β-ME). It is contemplated that additional factors may be added to the cell differentiation environment, including, but not limited to, fibronectin, laminin, heparin, heparin sulfate, retinoic acid, members of the epidermal growth factor family (EGFs), members of the fibroblast growth factor family (FGFs) including FGF2 and/or FGF8, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin, high dose activin, and amnionless. TGF/BMP/GDF antagonists could also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage. Other growth factors may include members of the insulin like growth factor family (IGF), insulin, the wingless related (WNT) factor family, and the hedgehog factor family. Additional factors may be added to promote mesendoderm stem/progenitor, endoderm stem/progenitor, mesoderm stem/progenitor, or definitive endoderm stem/progenitor proliferation and survival as well as survival and differentiation of derivatives of these progenitors.

In certain embodiments, the cell culture environment comprises plating the cells in an adherent culture. As used herein, the terms "plated" and "plating" refer to any process that allows a cell to be grown in adherent culture. As used herein, the term "adherent culture" refers to a cell culture system whereby cells are cultured on a solid surface, which may in turn be coated with a solid substrate that may in turn be coated with another surface coat of a substrate, such as those listed below, or any other chemical or biological material that allows the cells to proliferate or be stabilized in culture. The cells may or may not tightly adhere to the solid surface or to the substrate. The substrate for the adherent culture may comprise any one or combination of polyomithine, laminin, poly-lysine, purified collagen, gelatin, fibronectin, tenascin, vitronectin, entactin, heparin sulfate proteoglycans, poly glycolytic acid (PGA), poly lactic acid (PLA), and poly lactic-glycolic acid (PLGA). Furthermore, the substrate for the adherent culture may comprise the matrix laid down by a feeder layer, or laid down by the pluripotent human cell or cell culture. As used herein, the term "extracellular matrix" encompasses solid substrates such as but not limited to those described above, as well as the matrix laid down by a feeder cell layer or by the pluripotent human cell or cell culture. In one embodiment the cells are plated on matrigel coated plates. In another embodiment, the cells are plated on fibronectin coated plates. In certain embodiments, if the cells are plated on fibronectin, the plates are prepared by coating with 10 µg/ml human plasma fibronectin (Invitrogen, #33016-015), diluted in tissue grade water, for 2-3 hours at room temperature.

The methods of the present invention contemplate that cells are cultured in conditions that are essentially free of a feeder cell or feeder layer. As used herein, a "feeder cell" is a cell that grows in vitro, that is co-cultured with a target cell and stabilizes the target cell in its current state of differentiation. As used herein, a "feeder cell layer" can be used interchangeably with the term "feeder cell." As used herein, the term "essentially free of a feeder cell" refers to tissue culture conditions that do not contain feeder cells, or that contain a de minimus number of feeder cells. By "de minimus", it is meant that number of feeder cells that are carried over to the instant culture conditions from previous culture conditions where the pluripotent cells may have been cultured on feeder cells. In one embodiment of the above method, conditioned medium is obtained from a feeder cell that stabilizes the target cell in its current state of differentiation. In another embodiment, the defined medium is a non-conditioned medium, which is a medium that is not obtained from a feeder cell.

As used herein, the term "stabilize" refers to the differentiation state of a cell. When a cell or cell population is stabilized, it will continue to proliferate over multiple passages in culture, and preferably indefinitely in culture; additionally, each cell in the culture is preferably of the same differentiation state, and when the cells divide, typically yield cells of the same cell type or yield cells of the same differentiation state. Preferably, a stabilized cell or cell population does not further differentiate or de-differentiate if the cell culture conditions are not altered, and the cells continue to be passaged and are not overgrown. Preferably the cell that is stabilized is capable of proliferation in the stable state indefinitely, or for at least more than 2 passages. Preferably, it is stable for more than 3 passages, 4 passages, 5 passages, 6 passages, 7 passages, 8 passages, 9 passages, more than 10 passages, more than 15 passages, more than 20 passages, more than 25 passages, or most preferably, it is stable for more than 30 passages. In one embodiment, the cell is stable for greater than approximately 1 month, 2 months, 3 months, 4 months, 5 months, 6 months, 7 months, 8 months, 9 months, 10 months, or 11 months of continuous passaging. In another embodiment, the cell is stable for greater than approximately 1 year of continuous passaging. In one embodiment, stem cells are maintained in culture in a pluripotent state by routine passage in the defined medium until it is desired that they be differentiated. As used herein, the term "proliferate" refers to an increase in the number cells in a cell culture.

The compositions described herein are useful for the screening of test compounds to determine whether a test compound modulates pluripotency, proliferation, and/or differentiation of hESCs. Pluripotency, proliferation and/or differentiation of hESCs can be readily ascertained by one of ordinary skill in the art. Non-limiting methods include examining cell morphology, the expression of various markers, teratoma formation, and cell counts.

The progression of the HiFSC culture to the desired cell lineage, or its maintenance in an undifferentiated state can be monitored by quantitating expression of marker genes characteristic of the desired cell lineage as well as the lack of expression of marker genes characteristic of hESCs and other cell types. One method of quantitating gene expression of such marker genes is through the use of quantitative PCR (Q-PCR). Methods of performing Q-PCR are well known in the art. Other methods that are known in the art can also be used to quantitate marker gene expression. Marker gene expression can be detected by using antibodies specific for the marker gene of interest.

It is contemplated that the pluripotent cells can be passaged using enzymatic, non-enzymatic, or manual dissociation methods prior to and/or after contact with the defined medium of the invention. Non-limiting examples of enzymatic dissociation methods include the use of proteases such as trypsin, collagenase, dispase, and accutase. In one embodiment, accutase is used to passage the contacted cells. When enzymatic passaging methods are used, the resultant culture can comprise a mixture of singlets, doublets, triplets, and clumps of cells that vary in size depending on the enzyme used. A non-limiting example of a non-enzymatic dissociation method is a cell dispersal buffer. Manual passaging techniques have been well described in the art, such as in Schulz et al., 2004 Stem Cells, 22(7):1218-38. The choice of passaging method is influenced by the choice of extracellular matrix, and is easily determined by one of ordinary skill in the art.

The present invention also provides methods of producing an embryonic stem cell culture that is capable of being stably maintained in a modified defined culture medium comprising the steps of: a) introducing into an embryonic stem cell a vector comprising a nucleic acid that encodes an Erbb2 receptor that has a mutation in the region of Exon 15 to Exon 17 of the Erbb2 receptor; and b) growing the embryonic stem cells in a modified defined culture medium; wherein the modified defined culture medium comprises a basal salt nutrient solution, bFGF, IGF-I, and Activin A, and wherein the composition is essentially serum free and wherein the composition does not comprise heregulin. In a preferred embodiment, the Erbb2 receptor is Erbb2Δ16.

The present invention also provides methods of treating a patient having a tumor that expresses the Erbb2 receptor comprising administering to said patient an antibody in an amount effective to eliminate or reduce the patient's tumor, wherein the antibody binds specifically to an Erbb2 receptor that has a mutation in the region of Exon 15 to Exon 17 of Erbb2 or to an Erbb2 isoform that differs in its glycosylation profile from a wild type Erbb2 isoform. In certain embodiments, the antibody binds specifically to an Erbb2Δ16 receptor. In some embodiments, the carcinoma is selected from the group consisting of renal carcinoma, human breast carcinoma, gastric carcinoma, and salivary gland carcinoma. In other embodiments, the tumor is selected from the group consisting of a large-cell, comedo growth type of ductal carcinoma, ovarian cancer, prostate cancer, acute lymphoblastic leukemia, bladder cancer, cervical cancer, childhood medulloblastoma, colorectal cancer, oral squamous cell carcinoma, germ-cell testicular cancer, cholangiocarcinoma, lung cancer, osteosarcoma, pancreatic adenocarcinoma, primary fallopian tube carcinoma, and synovial sarcoma. The invention contemplates that in some embodiments, the methods may involve administering a therapeutically effective amount of a liposome comprising said antibody. As used herein, the term "liposome" refers to a fluid-filled pouch whose walls are made of layers of phospholipids and that is used to deliver the cytotoxic compound and/or Erbb2 antibody to a specific location. The liposomes help to shield healthy cells from the drugs' effects and to prevent their concentration in vulnerable tissues, lessening or eliminating the common side effects of nausea, fatigue, and hair loss. The liposome may be coated with the antibody and may be filled with a cytotoxic compound.

Antibodies can be made by many well-known methods (See, e.g., Harlow and Lane, "Antibodies; A Laboratory Manual," Cold Spring Harbor Laboratory, Cold Spring Harbor, N.Y., (1988)). Briefly, nucleic acids encoding the Erbb2 isoform are introduced into a cell in which the Erbb2 isoform may be expressed on the surface of the cell. The cells expressing the Erbb2 isoform can be injected into an animal in an amount and in intervals sufficient to elicit an immune response. Antibodies can either be purified directly, or spleen cells can be obtained from the animal. The cells can then be fused with an immortal cell line and screened for antibody secretion. The antibodies can be used to screen nucleic acid clone libraries for cells secreting the antigen. Those positive clones can then be sequenced. (See, for example, Kelly et al., 1992, Bio/Technology 10:163-167; Bebbington et al., 1992, Bio/Technology 10:169-175). Alternatively, a purified antigen may be used in some instances to inoculate the animals.

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in the Examples below. Alternatively, see Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988.

The compositions of this invention further contain a pharmaceutically acceptable carrier. The phrases "pharmaceutically or pharmacologically acceptable" refer to molecular entities and compositions that do not produce an adverse, allergic, or other untoward reaction when administered to an animal, or a human, as appropriate. Veterinary uses are equally included within the invention and "pharmaceutically acceptable" formulations include formulations for both clinical and/or veterinary use. As used herein, "pharmaceutically acceptable carrier" includes any and all solvents, dispersion media, coatings, antibacterial, and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions is contemplated. For human administration, preparations should meet sterility, pyrogenicity, and general safety and purity standards as required by FDA Office of Biologics standards. Supplementary active ingredients can also be incorporated into the compositions.

As used herein with respect to these methods, the term "administering" refers to various means of introducing a composition into a cell or into a patient. These means are well known in the art and may include, for example, injection; tablets, pills, capsules, or other solids for oral administration; nasal solutions or sprays; aerosols, inhalants; topical formulations; liposomal forms; and the like. As used herein, the term "effective amount" refers to an amount that will result in the desired result and may readily be determined by one of ordinary skill in the art.

The antibody compositions of the present invention may be formulated for various means of administration. As used herein, the term "route" of administration is intended to include, but is not limited to subcutaneous injection, intravenous injection, intraocular injection, intradermal injection, intramuscular injection, intraperitoneal injection, intratracheal administration, epidural administration, inhalation, intranasal administration, oral administration, sublingual administration, buccal administration, rectal administration, vaginal administration, and topical administration. The preparation of an aqueous composition that contains such an Erbb2 antibody or antibody fragment as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The antibody compositions of the present invention can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars, or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate, and gelatin.

Prior to or upon formulation, the antibody compositions of the present invention should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filter sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the active ingredient (e.g. Erbb2 antibody or antibody fragment) admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that for human administration, preparations should meet sterility, pyrogenicity, and general safety and purity standards as required by FDA Office of Biological Standards.

Throughout this application, various publications are referenced. The disclosures of all of these publications and those references cited within those publications in their entireties are hereby incorporated by reference into this application in their entirety in order to more fully describe the state of the art to which this invention pertains.

EXAMPLES

Example 1 hESCs as a Model for Transformation of Tissue Progenitor Cells

The inventors have isolated and characterized four NIH-registered hESCs lines that were used for these studies: BG01, BG02, BG03, and BG01v.

While hESCs can exhibit genomic stability over prolonged culture in vitro, characteristic genetic changes can occur when hESCs are maintained under certain conditions. The most common alterations observed include trisomies of chromosomes 12, 17, or 17q. A stable karyotypic variant of BG01 was isolated, termed BG01v (49 XXY, +12, +17), which due to ease of culturing is a useful HESC line for experimental analysis. These trisomies also are found in naturally occurring testicular teratocarcinomas and the embryonal carcinoma cells (EC) derived from them. EC cells likely represent transformed derivatives of gonadal germ cells and are highly related to embryonic stem cells. This suggests that overlapping molecular pathways are altered in both pluripotent cell types by these common aneuploidies.

BG01v cells were obtained by repeatedly breaking human ES cell colonies down to single cells and replating them. Normal ES cells typically show very poor survival when plated as single cells, and therefore selection pressure apparently leads to the generation of more robust lines that are able to withstand this process. Because hESCs can be maintained as a relatively homogeneous culture of pluripotent cells in vitro, the changes that can occur to hESCs in culture could be a highly relevant model for examining the molecular controls of rare tissue specific progenitor cell self-renewal or tumorigenesis. While the BG01v cell line exhibited altered growth properties and could grow independently of exogenous heregulin, it was not overtly transformed but exhibited key characteristics of pluripotency, including marker expression and spontaneous differentiation potential in vitro. This is unlike most EC cells, which often lose the potential to differentiate to some lineages, or the capacity to undergo spontaneous differentiation. This suggests that the changes that occurred in selecting for these trisomies in BG01v cells could represent very early transforming events. Variant hESCs exhibited growth advantages that are associated with robust plating, survival, and resistance to apoptosis. One of the most apparent differences to normal cells was the presence of small pockets of undifferentiated OCT4+ cells in teratomas made from BG01v cells. Some of these residual pluripotent cells (termed BG01vT cells) have been isolated and expanded, and these cells were shown to retain other markers of hESCs. These cells were not recovered from teratomas made from the same doses of normal hESCs.

These results suggest that BG01v cells represent a pre-cancerous state that mimics events in the formation of certain tumors, and that BG01vT cells contain additional mutations that transform normal stem cells into CSCs. This series of pluripotent cell types (i.e. BG01 to B01v to BG01vT to EC cells) may represent progressive stages in a stepwise progression towards tumorigenesis (i.e. tissue progenitor cells to pre-cancerous progenitor cells to CSCs to highly transformed CSCs). Accordingly, studying human ES cells and the variant BG01v cells (whose karyotype is stable in culture) will be invaluable to study the formation of CSCs and to study the signaling pathways important for self-renewal (i.e. maintenance of the stem cell state).

Example 2

Characterization of Modified Defined Culture Medium for Producing Cancer Stem Cells Parent cultures were maintained as described previously (Schulz et al., 2003, BMC Neurosci., 4:27; Schulz et al., 2004, Stem Cells, 22(7):1218-38; Rosler et al., 2004, Dev, Dynamics, 229:259-274; Brimble et al., 2004 Stem Cells Dev., 13:585-596). Briefly, the cells were grown in dishes coated with Matrigel or fibronectin, in conditioned media from MEFs (MEF-CM) comprising DMEM:F12 with 20% KSR, 8 ng/ml FGF2, 2 mM L-Glutamine, 1× non-essential amino acids, 0.5 U/ml penicillin, 0.5 U/ml streptomycin, 0.1 mM β-mercaptoethanol (Sigma) with collagenase passaging.

The defined culture (DC) media characterized previously comprised DMEM/F12, 2 mM Glutamax, 1× non-essential amino acids, 0.5 U/ml penicillin, 0.5 U/ml streptomycin, 10 μg/ml transferrin (all from Invitrogen) 0.1 mM P-mercaptoethanol (Sigma), 0.2% fatty acid-free Cohn's fraction V BSA (Serologicals), 1× Trace Element mixes A, B, and C (Cellgro), and 50 μg/ml Ascorbic Acid (Sigma). Variable levels of recombinant growth factors were used, including FGF2 (Sigma), LongR3-IGF1 (JRH Biosciences), Heregulin-β EGF domain (HRGβ, Peprotech), TGFβ (R&D systems), nodal (R&D systems), LIF (R&D systems), EGF (R&D systems), TGFα (R&D systems), HRGα (R&D systems), BMP4 (R&D systems), and Activin A (R&D Systems). LongR3-IGF1 is a modified version of IGF1 that has reduced affinity for IGF1 binding proteins, some of which are expressed in hESCs.

By contrast, the modified defined condition (MDC) media used herein, was as described in the previous paragraph, however, the MDC media did not include Heregulin. heregulin signals via an ErbB2/ErbB3 cell surface receptor heterodimer that is part of a PI3K driven signaling pathway (heregulin actually binds to ErbB3 which in turn heterodimerizes with ErbB2 leading to signaling through the ErbB2 tyrosine kinase). This pathway is aberrantly regulated in many different forms of solid tumors (e.g. breast cancers, colorectal cancers, prostate cancers, ovarian cancers). Therefore, cell cultures capable of growing in this MDC media are likely to have abnormal signaling occurring in the absence of the Erbb2 ligand heregulin.

Matrigel coated dishes were prepared by diluting Growth Factor Reduced BD matrigel matrix (BD Biosciences) to a final concentration of 1:30 or 1:200 in cold DMEM/F-12. 1 ml/35 mm dish was used to coat dishes for 1-2 hours at room temperature or at least overnight at 4° C. Plates were stored up to one week at 4° C. Matrigel solution was removed immediately before use.

BG01v cells obtained as described above are capable of stable maintenance in the presently described MDC media. These cells are a highly relevant model for examining the molecular controls of tissue specific progenitor cell self-renewal or tumorigenesis.

Furthermore, additional variant hESCs can be generated, so that experiments using variant cells can be confirmed with multiple lines. Normal BG01 and BG03 cells are deliberately split to single cell suspensions and grown in undefined media. Cultures maintained in this way are expected to develop trisomies. Several parallel cultures are maintained for approximately 5 passages, then karyotyped. Cultures that show trisomy of chromosome 17 or 17q are used for additional analyses to confirm results generated with the BG01v line. Moreover, additional cell lines useful for such studies are created by utilizing cells of a primary tumor and culturing in the same manner as described above.

Example 3

Expression of the Erbb2 and Erbb2Δ16 Transcripts

The inventors suggested that the BG01v cell line up-regulated Erbb2 signaling, leading to more robust culture and independence of exogenous heregulin in the media. To test this suggestion, the inventors engaged the assistance of Frank Jones (Tulane University), and the inventors performed additional experiments without Dr. Jones's assistance as well.

Dr Jones previously demonstrated that the Erbb2Δ16 transcript was found to be expressed at a fraction of the level of wild type Erbb2 transcript on a tissue-wide level in primary breast tumors. It has also been shown that Erbb2 μl 6 expression promoted increased invasion in models of breast cancer, based on the over-expression of an Erbb2Δ16 transgene. This system was used to show that the Herceptin® antibody can bind to Erbb2Δ16, but does not inactivate signaling of this complex (Castiglioni et al., 2006, Endocrine Related Cancer, 13:221-232). These data suggest that there are fundamental differences in the signaling of this variant Erbb2. Dr Jones also had shown that Erbb2Δ16 expression is not found in normal tissues, but was associated with multiple other tumor types, including ovarian, prostate, and colorectal cancers. These data suggest that Erbb2Δ16 expression and associated effects on cell signaling may be important oncogenic factors in several types of cancer.

The inventors performed the following experiments independently. To determine if normal hESCs express wild type Erbb2 and variant hESCs primarily Erbb2Δ16, quantitative PCR was used. A clear difference between expression of Erbb2Δ16 mRNA in normal and variant cells would suggest a transcriptional switch in the populations and perhaps a typical "mutation." However, the inventors have shown that both normal and variant hESCs express the Erbb2Δ16 transcript (FIG. 2). There were no substantial differences in wild type Erbb2 and Erbb2Δ16 expression in normal hESCs and BG01v cells grown in parental or defined conditions. Furthermore, there were no substantial differences in the ratio of Erbb2Δ16:wild type Erbb2 expression. This data suggests that the growth factor independence exhibited by BG01v cells was not related to over-expression of Erbb2 or Erbb2Δ16. It remains possible that there are differences in translation of these Erbb2 isoforms between normal and variant hESCs. This may be due to changes in polyadenylation of the message, other splicing changes to the Erbb2Δ16 transcript (and potential translational control elements), or other known translational control mechanisms. Any such control system is a candidate target for therapy development (e.g. small molecules, or RNAi) that specifically inhibits the production of Erbb2Δ16 or other transforming isoforms of this protein.

Example 4

Analysis of Expression of the Erbb2 and Erbb2Δ16 Proteins

The differential expression of Erbb2 protein isoforms was analyzed by Western blotting (FIG. 3). BG02 and BG01v cells were grown in defined conditions containing HRG, LR-IGF1, FGF2, and Activin A. Protein lysates were separated by 6% PAGE under reducing (Panel A) and non-reducing (Panel B) conditions. 30 μg of BG02 and BG01v lysates were loaded separately, and a 50:50 mix of these samples (15 μg each) were run in the third lane. The blots were probed with an anti-Erbb2 antibody. Under reducing conditions, Erbb2 was detected predominantly as an approximately 185 kDa band in both BG02 and BG01v samples. However, this band appeared to be broader in the BG02 sample, suggesting a difference in migration of this protein in the BG01v sample. This difference could reflect the predominant expression of a smaller isoform, such as Erbb2Δ16, or a change in the profile of post-translational modifications of Erbb2, in BG01v cells. Under non-reducing conditions, a high molecular weight band of greater than 300 kDa was observed in both samples (arrowhead). This band could represent the disulfide-linked Erbb2Δ16 homodimer. This band appeared to represent only a small fraction of the total Erbb2 in both BG02 and BG01v samples.

The same samples as in (Panel A) were separated by 6% PAGE, but were run further to increase the separation of large molecules (Panel C). Probing the blot with the same anti-Erbb2 antibody revealed migration differences between normal B02 and BG01v cells. A predominant slow-migrating band(s) in the B02 cells (arrowhead) was substantially reduced in BG01v cells. The differences observed between normal and variant cells may indicate differences in the expressed isoforms of Erbb2, or differences in glycosylation or other post-translational modifications, which is addressed in the following example.

These data were the first demonstration of endogenous Erbb2Δ16 dimers in a stem cell population. Expression of the Erbb2Δ16 protein may be shown by immunoprecipitating with a general Erbb2 antibody followed by trypsin digestion and mass spec analysis. This will formally identify the endogenous Erbb2Δ16 protein in BG01v cells, by demonstrating the presence of a trypsin fragment that spans the exon 15-17 junction.

Western blotting showed differences in migration in Erbb2 isoforms between normal and variant hESCs and demonstrated that there were molecular differences between the Erbb2 present in these cells. This is consistent with the differences in growth factor dependence demonstrated by normal or variant cells in the defined media, and the effect of Erbb2 TK inhibitors on BG01v cells. This data suggested strongly that a major functional difference between normal and variant hESCs is expression of different Erbb2 isoforms, examples of such variant isoforms include Erbb2Δ16 and different post-translationally modified isoforms of Erbb2.

In addition, the inventors predict that wild type Erbb2 and Erbb2Δ16 will differ in processing by ectodomain shedding. Ectodomain shedding by ADAM proteases releases the extracellular region of Erbb2 (ECD) and creates a membrane tethered, N-terminal truncated p95 isoform (Yuan et al., 2003, Prot. Exp. Pur., 29:217-222). The Erbb2p95 isoform is thought to be constitutively active, whereas the ECD is thought to be able to compete with membrane bound Erbb2 for soluble ligand. Higher Erbb2 ectodomain concentrations have been correlated with poorer clinical outcome in breast cancer (Christianson et al., 1998, Cancer Res., 58:5123-5129). The cleavage site for ectodomain shedding is present within exon16 (Yuan et al., 2003, Prot. Exp. Pur., 29:217-222), and therefore, it is predicted that Erbb2Δ16 cannot be processed in the same way. While these predictions need to be tested, differences in ectodomain shedding between normal and variant hESCs related to Erbb2Δ16 or other isoforms, are likely to have a biological outcome. The overall effect of these changes to Erbb2 in variant hESCs is constitutive activation of Erbb2 signaling associated with trisomy of 17q, and development of a growth factor independent pre-cancerous state. This also demonstrated the value of using hESCs to examine the molecular pathways that control the growth or transformation of tissue specific progenitor cells.

Erbb2Δ16 is likely a central mediator of multiple cancers, and the primary action of Erbb2Δ16 is likely to transform tissue specific progenitor cells and generate CSCs. Because BG01v cells appear to express Erbb2Δ16 and/or other different post-translational modified Erbb2 isoforms, the inventors suggest that these isoforms are a major determinant in the transformation of progenitor cells of breast epithelia. As these cells differentiate, these Erbb2 isoforms are down-regulated, and therefore only appear to have a minor contribution on a population wide basis.

Example 5

Analysis of Erbb3 Expression

Figure 4:
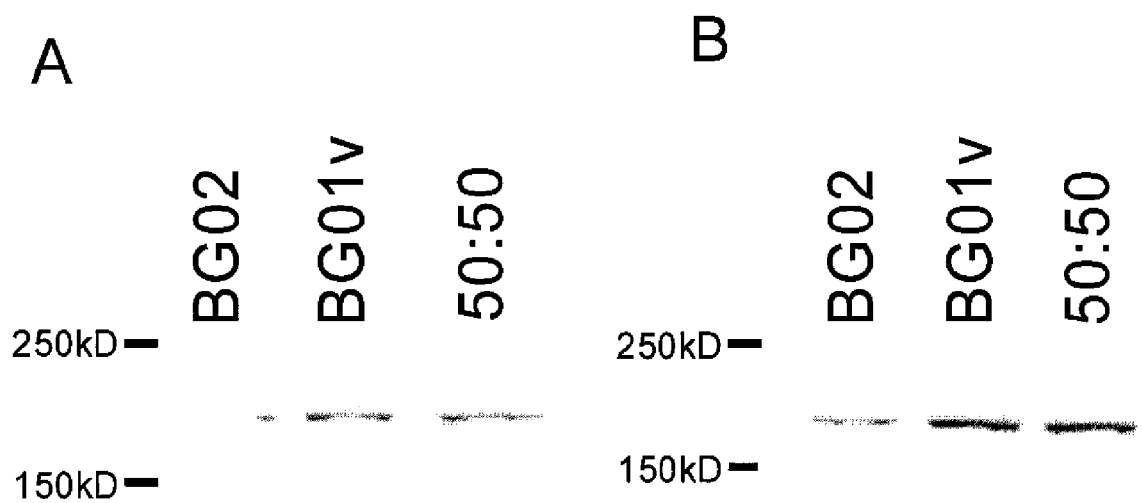
FIGS. 4A and 4B show Western blotting of Erbb3 in hESCs. BG02 and BG01v cells were grown in defined conditions containing HRG, LR-IGF1, FGF2, and Activin A. Protein lysates were separated by 6% PAGE under reducing (Panel A) and non-reducing (Panel B) conditions. 30 ug of BG02 and BG01v lysates were loaded separately, and a 50:50 mix of these samples (15 ug each) were run in the third lane. The blots were probed with an anti-Erbb3 antibody.

FIGS. 4A and 4B show Western blotting of Erbb3 in hESC. B02 and BG01v cells were grown in defined conditions containing HRG, LR-IGF1, FGF2, and Activin A. Protein lysates were separated by 6% PAGE under reducing (Panel A) and non-reducing (Panel B) conditions. 30 µg of B02 and B01v lysates were loaded separately, and a 50:50 mix of these samples (15 µg each) were run in the third lane. The blots were probed with an anti-Erbb3 antibody.

Under reducing conditions, Erbb3 was detected as a 185 kDa band in both BG02 and BG01v samples. BG01v cells appeared to express an elevated level of Erbb3 as compared to normal BG02 cells. A similar result was observed under non-reducing conditions. Unlike Erbb2, Frbb3 migrated as a tight band, suggesting that it was a homogeneous species and differing splice variants or post-translational modifications were not evident.

Example 6

Analysis of Posttranscriptional Modification of Erbb2 and Erbh2Δ16

One possible reason for the difference in migration of the Erbb2 and Erbb2Δ16 proteins on polyacrylamide gel is that the proteins have different levels of post-translational modification. There are 7 predicted extracellular consensus sites for N-linked glycosylation (Asn-x-Ser/Thr) in Erbb2. Two of these sites contain a cysteine (Asn-Cys-Ser, and Asn-Cys-Thr), and one of these is located 5 amino acids upstream from Exon 16. There are no predictable O-linked sites in the protein.

Figure 5:
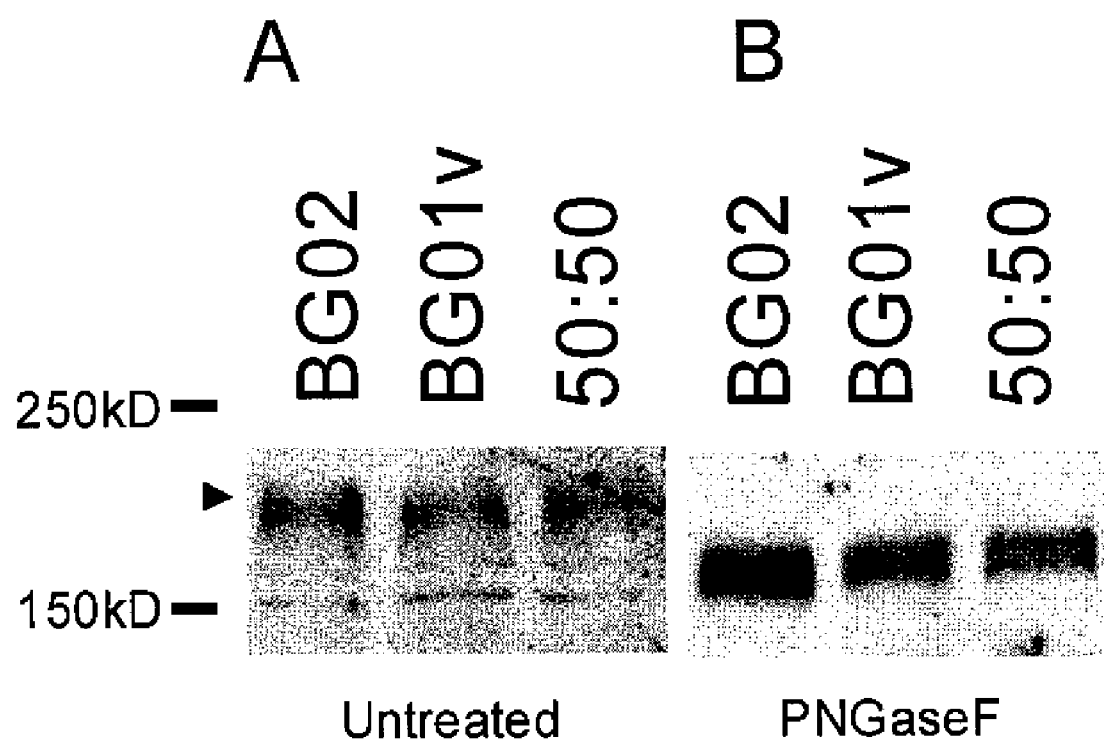
FIGS. 5A and 5B show Western blotting of Erbb2 following treatment to remove N-linked glycosylation. BG02 and BG01v cells were grown in defined conditions containing HRG, LR-IGF1, FGF2, and Activin A. Protein lysates (Panel A), or lysate deglycosylated with PNGaseF (Panel B), were separated by 6% PAGE under reducing conditions. 30 ug of BG02 and BG01v lysates were loaded separately, and a 50:50 mix of these samples (15 ug each) were run in the third lane.

FIGS. 5A and 5B show Western blotting of Erbb2 following treatment to remove N-linked glycosylation. BG02 and BG01v cells were grown in defined conditions containing HRG, LR-IGF1, FGF2, and Activin A. Protein lysates (Panel A), or lysate deglycosylated with PNGaseF (Panel B), were separated by 6% PAGE under reducing conditions. 30 µg of BG02 and BG01v lysates were loaded separately, and a 50:50 mix of these samples (15 µg each) were run in the third lane.

PNGaseF removes N-linked glycosylation, and the reaction was performed overnight in lysis buffer containing 0.2% NP-40. The blots were probed with an anti-Erbb2 antibody. As shown previously, differences in the migration of Erbb2 were apparent between normal BG02 and BG01v cells in the untreated samples. A predominant slow-migrating band(s) in the BG02 cells (arrowhead) was altered in BG01v cells, with faster migrating bands being more prominent in the BG01v sample. Deglycosylation of N-linked oligosaccharides with PNGaseF resulted in faster migrating bands in both samples. An apparent approximately 150 kDa migrating dimer resulted, and was similar, in both samples. This indicated that differences in N-linked glycosylation of Erbb2 were responsible for some of the differences observed between normal and variant hESCs. Other post-translational modifications to Erbb2 are expected, because the predicted molecular weight of the protein is only 137.9 kDa. However, as the PNGaseF treated samples were apparently similar, other types of post-translational modifications may not be different between normal and variant hESCs.

In addition, wild type Erbb2 can be processed, and the ectodomain is shed. The processing site is located within exon 16, and therefore the delta 16 variant cannot be processed in this way.

Example 7

Use of Expression of Erbb2Δ16 to Enable hESCs to Become Independent of Heregulin A mammalian expression plasmid was constructed that will constitutively express Erbb2Δ16 protein in hESCs under the control of a CMV promoter. This plasmid is transfected into normal BG02 hESCs using lipofection. Stable transfectants are selected with G-418 resistance, expanded, and karyotyped. Expression of Erbb2Δ16 is confirmed by western blotting using an introduced C-terminal FLAG epitope. This experiment will likely show that Erbb2Δ16 enables karyotypically normal hESCs to become independent of heregulin (Erbb2 activating growth factor). The Erbb2 TK inhibitors will still inhibit the growth of these cells, demonstrating that Erbb2Δ16 is a key pathway in self-renewal. Erbb2Δ16 expressing normal hESCs can be injected into SCID mice to make teratomas. Analysis of teratoma sections will likely show that pockets of Oct4+ cells are present, demonstrating that Erbb2Δ16 expression is an early transformation event in hESCs. These residual stem cells can be isolated from teratomas, expanded in culture, and karyotyped to see if aneuploidies have arisen. These cells can be re-injected into mice to make new teratomas. This will likely demonstrate that these small pockets of Oct4+ cells are representative of CSCs, and that this is caused by Erbb2Δ16 expression.

Example 8

Use of RNAi to Inhibit Expression of Erbb2Δ16

BG01v cells are transfected with plasmids that reduce the level of Erbb2Δ16 mRNA, and subsequently, protein, by RNAi. This may cause the cells to die, or to revert to becoming dependent on heregulin (i.e. normal signaling through Erbb2/Erbb3). If these cells can be maintained, they can be injected into SCID mice to make teratomas. The teratomas can be analyzed by histology and immunohistochemistry (IHC).

This data will likely show that inhibiting Erbb2Δ16 will deplete the numbers of pluripotent cells found in tumors made from BG01v cells. This will demonstrate that the Erbb2Δ16 "mutation" is a central event in the transformation of hESCs, but that inhibition of Erbb2Δ16 will suppress the "precancerous" state of variant hESCs. Similar experiments can be performed by implanting BG01v cells to SCID mice, then exposing the mice to some of the Erbb2 TK inhibitors. This may slow the growth of the tumor, or cause reduction in some of the differentiated lineages (i.e. those that are dependent on Erbb2 signaling during differentiation). The main effect characterized will likely be that these inhibitors will reduce the pockets of Oct4+ cells. These RNAi and Erbb2 TK inhibitor studies are complementary to and can confirm the studies that over-express Erbb2 μl 6 in normal cells.

Example 9

Production of Monoclonal Antibodies Specific for Erbb2Δ16

Monoclonal antibodies that specifically recognize the disulfide linked Erbb2Δ16 homodimer, an Erbb2Δ16/Erbb3 heterodimer, or post-translational modifications of Erbb2 that are specific to variant hESCs (or some other epitope that is not present in the wild type Erbb2 protein) are generated. In particular, the monoclonal antibodies may detect a specific difference in glycosylation levels of the Erbb2Δ16 protein, or other Erbb2 isoforms, as compared to the wild type Erbb2 protein. Such distinctions are possible as has been demonstrated previously (Johns et al., 2005, FASEB J 19:780-82).

The antibodies are generated by immunizing mice with a mouse cell line that has been transfected with the Erbb2Δ16 expression plasmid (i.e. Erbb2Δ16 will be in its native conformation), both Erbb2Δ16 and Erbb3, or other relevant isoforms of Erbb2. The mice are boosted several times. Monoclonal antibodies that specifically react to mouse cells expressing human Erbb2Δ16, or other isoforms, but not wild type Erbb2 are identified by this screening process. Approximately 50-100 monoclonal antibodies to Erbb2 isoforms can be generated by this process. The antibodies are tested to determine which ones recognize the disulfide linked Erbb2Δ16 homodimer, Erbb2Δ16/Erbb3 heterodimer, or specific epitope. These antibodies are highly valuable reagents and can be used to determine where the Erbb2Δ16 protein is found in the body. This will show that Erbb2Δ16 is only expressed in CSCs. Erbb2Δ16 will be expressed in numerous types of CSCs, including in breast, ovarian, colorectal, and prostate CSCs.

The antibodies can be used to target a cytotoxic compound to cells, expressing the disulfide linked Erbb2Δ16 homodimer, Erbb2Δ16/Erbb3 heterodimer, or specific epitope. Potential cytotoxic agents include, among others, molecules such as diptheria toxin, radiochemicals, or cytotoxic compounds (Doronina et al., 2006, Bioconjugate Chem. 17:114-24; Lambert, 2005, Curr. Opin. Pharm., 5:543-549). The killing of cells expressing a hESC variant-specific epitope can be tested in vitro, in the described teratoma model, then in other animal models of tumorigenesis that involve Erbb2 μl 6 or other Erbb2 isoforms.

Example 10

Serial Transplantation of BG01vT Cells

BG01vT cells can be expanded, characterized, and re-injected to SCID mice to generate teratomas. The proportion of Oct4+ cells in teratomas can be examined and compared to that seen in previous experiments using BG01v cells. BG01vT cells can be extracted from tumors, characterized, and this experiment can be repeated serially. The experiment will show that BG01vT cells represent a CSC niche in BG01v teratomas, and can regenerate tumors. This analysis will also show that BG01vT cells undergo progressive alterations in serial tumors. A greater proportion of cells may remain undifferentiated in serially passaged tumors, which has been observed in testicular teratocarcinomas and EC cells. One interpretation of this is that there is an accumulation of mutations that progressively influence the selection of self-renewing pluripotent cells, reflected as increased malignancy of these cells. Serial passaging of BG01vT cells also represents a model for metastasis of CSC in HESC teratomas. This will demonstrate that normal hESCs form "benign teratomas", which do not show a CSC niche, whereas variant hESCs generate tumors with transplantable CSC and may therefore be considered as malignant teratocarcinomas.

Example 11

Response of hESCs to the Developing Mammary Microenvironment

To examine if there is a functional similarity between normal hESCs and mammary progenitor cells, undifferentiated hESCs can be transplanted to the developing mammary epithelia. If the similarities between these stem cells are significant, hESCs will respond to the cues of this microenvironment and differentiate to mammary tissue. The epithelium-free mammary fat pad model is a well established approach for xenograft transplantation and differentiation of mammary cells (McDaniel et al., Am J Path 2006, 168 Vol 2. Mehta et al., Breast Can. Res Treat 1993, 25:65-71). BG02, BG01v or BG02 expressing Erbb2Δ16 can be transplanted to the fat pad of mammary gland no. 4 of Nu/Nu athymic nude mice (NCI Frederick, Cat#01B74). Histology and IHC can be used to examine differentiation to mammary tissue, and the effects of trisomy chr17q or constitutive Erbb2Δ16 expression. If hESCs differentiate to mammary tissue, then it will be clear that they responded correctly to the developmental signals found in this tissue. This will clearly indicate that hESCs are functionally related to mammary tissue progenitor cells, and therefore also further link variant hESCs and mammary CSC.

Example 12

The Erbb2Δ16 Contains a Proline to Alanine Amino Acid Substitution in the C-terminus To isolate the Erbb2Δ16 cDNA clone, a nucleotide sequence encoding Erbb2a (FIG. 1) was used to screen a BG01 cDNA library. The Erbb2Δ16 cDNA isolate and deduced amino acid sequence are shown in FIGS. 6 and 7 (SEQ ID NO:2 and 3, respectively). FIG. 8 shows an amino acid sequence alignment comparing the ERBB2Δ16 (FIG. 7) and ERBB2a (FIG. 1) sequences. The sequences are substantially about 98% identical. The alignment demonstrates that the Erbb2Δ16 sequence ("D16") contains the 16 amino acid sequence deletion. See the bold and italicized region of the ERBB2a sequence in FIG. 8. Interestingly, there is also a proline to alanine amino acid substitution and/or change at amino acid position 1155 (bolded and underlined) of the ERBB2Δ16 sequence: AGATLERAKTLSPGK (SEQ ID NO:4). The change from proline to alanine may alter the tertiary structure of the mature ERBB2Δ16 protein, as proline is often involved in the bending regions of protein structures, and/or assert an effect on protein conformations.

The secondary and tertiary structure can be predicted based on an Erbb2 variant amino acid sequence, for example, the Erbb2Δ16 amino acid sequence (SEQ ID NO:3). Such methods, including computer generated methods for predicting secondary and/or tertiary structure are described herein in this invention.

Example 13

Altered Phosphorylation of ERBB2/3 in Variant hESCs

The alteration of migration of Erbb2 in BG01 variant (BG01v) cells as shown in FIG. 3 as compared to karyotypically normal hESCs (BG02), as well as the capacity of BG01v cells to grow in the absence of exogenous heregulin, suggested alterations to Erbb2 signaling. To assess the phosphorylation status of Erbb2 in normal and variant hESCs, BG01 and BG01v cells were assayed by phosphoblotting after treatment with different cell culture conditions.

Cells were maintained in steady state conditions in defined conditioned-heregulin/Activin A/IGF1/FGF (DC-HAIF), were incubated in media minus or starved of growth factors (e.g., no heregulin/Activin A/IGF1/FGF) overnight, or starved and then pulsed about 15 minutes with 10 ng/ml heregulin. Proteome Profiler™ human phospho-RTK antibody arrays (R&D Systems, Cat#ARY001) were used according to the manufacturer's instructions. Protein lysates were prepared in 1% NP-40, 20 mM Tris-HCl (pH 8.0), 137 mM NaCl, 10% glycerol, 2.0 mM EDTA, 1.0 mM sodium orthovanadate, 10 µg/ml Aprotinin, and 10 µg/ml Leupeptin. 500 µg fresh protein lysates were incubated overnight with nitrocellulose membranes dotted with duplicate spots for 42 anti-RTK antibodies and 5 negative control antibodies, as well as 8 anti-phosphotyrosine positive control spots. The arrayed antibodies capture the extracellular domains of both phosphorylated and unphosphorylated RTKs, and bound phospho-RTKs were detected with a pan anti-phospho-tyrosine antibody conjugated to horseradish peroxidase (HRP) using chemiluminescence. X-ray film was scanned and spots were quantified using NTH-image (world wide web at rsb.info.nih.gov/nih-image/). Blots were normalized using the 8 pan-antiphosphotyrosine antibody control spots per filter, and normalized values were averaged.

FIG. 9A shows that BG01v cells exhibited an altered profile of Erbb2 and Erbb3 phosphorylation compared to karyotypically normal BG01 cells (FIG. 9A). FIG. 9B shows that hyperphosphorylation of Erbb3 was observed in BG01v cells in steady state and starved conditions, indicating altered activation of Erbb2 (which trans-phosphorylates Erbb3), or stabilization of Erbb3, or similar related mechanism that involves up-regulated signaling via the Erbb2/3 heterodimer (FIG. 9B).

Example 14

Inhibition of Erbb2 Autophosphorylation Inhibits the Proliferation of hESCs

Figure 10:
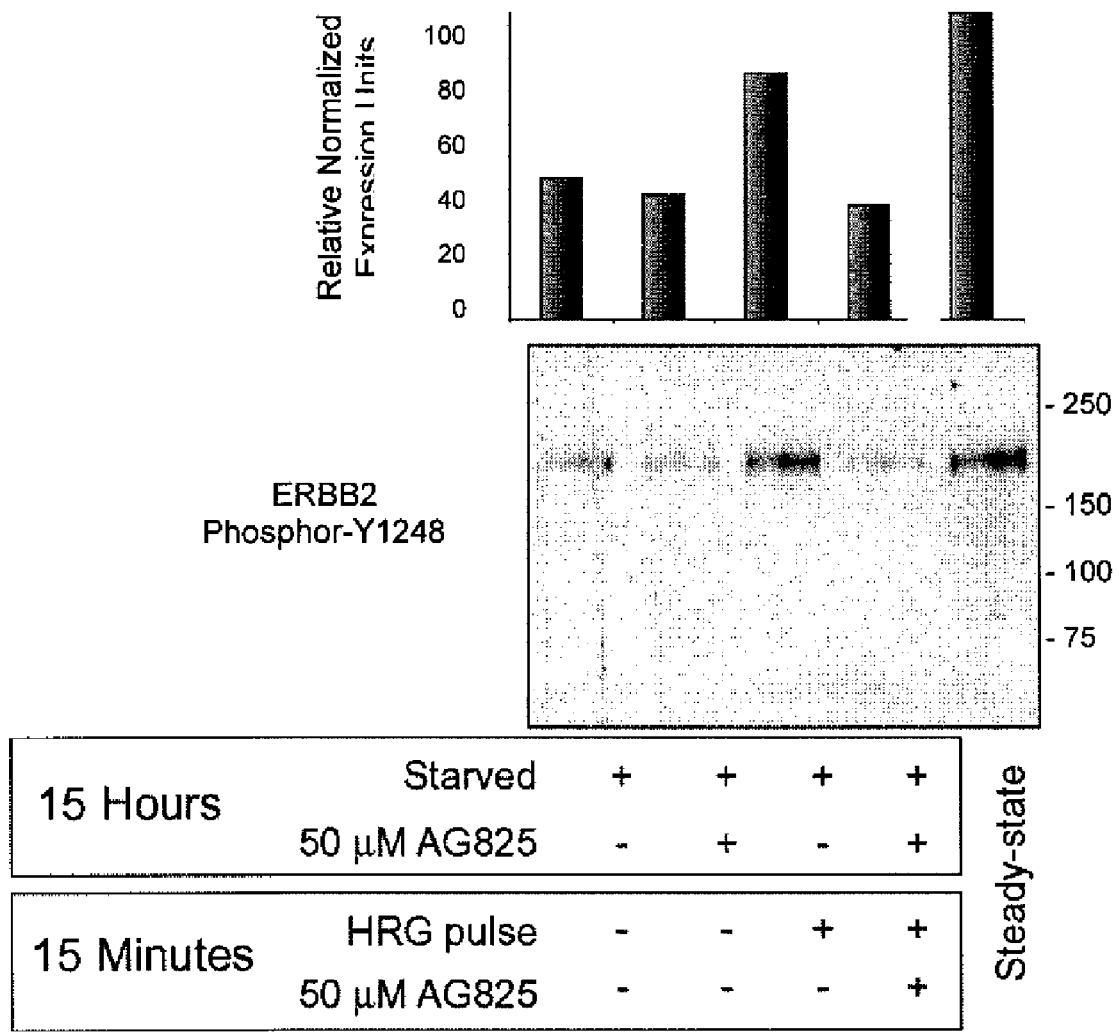
FIG. 10 shows AG825 inhibition of ERBB2 Y1248 phosphorylation in hESCs. BG01 hESCs were grown in DC-HAIF and then in media minus or starved of growth factors overnight, washed and then pulsed with either with heregulin (HRG) or not, or incubated with AG825 or not. Lane 1 shows starved hESCs but did not receive an HRG pulse; lane 2 shows starved hESCs and a pulse with media containing 50 μM AG825 (treatment control); lane 3 shows starved hESCs and received an 10 ng/mL HRG1β pulse (positive control); lane 4 shows starved hESCs and pulsed with 10 ng/mL HRG1β and 50 μM AG825; and lane 5 shows hESCs in DC-HAIF alone.

Tyrphostin AG825 is a highly selective inhibitor of the Erbb2 tyrosine kinase, (Murillo H, Schmidt L J, Tindall D J. Cancer Res. 2001; 61:7408-7412), and was used to investigate the role of Erbb2 in hESCs. AG825 significantly inhibited proliferation of hESCs growing in CM (FIG. 10).

All BG01 HESC cultures were first grown in defined conditioned-heregulin/Activin A/IGF1/FGF (DC-HAIF) and then in media starved of growth factors overnight e.g., no heregulin, Activin A, IGF1 and/or FGF. The cultures were then washed and treated as indicated in FIG. 10 (lanes 1-5). After an overnight incubation in media minus growth factors ("starved"), the cultures were washed and treated as indicated in FIG. 10. hESCs were untreated and received no heregulin pulse or AG825 (lane 1, negative control); hESCs were treated by a 15 minute pulse with media and 50 uM of the AG825 inhibitor (lane 2); hESCs were treated by a 15 minute pulse with media containing 10 ng/ml HRG1β ("HRG pulse"; lane 3); hESCs were treated with a 15 minute pulse with media containing 10 ng/ml HRG1β and 50 µM of the AG825 inhibitor (lane 4; positive control); and parental BG01 hESCs were treated with a 15 minute pulse with DC-HAIF media, which contains the heregulin/Activin A/IGF1/FGF growth factors ("steady state" positive control; FIG. 10; lane 5).

Cell lysates were prepared as per RTK blotting, separated by 4-20% gradient SDS-PAGE, blotted and detected with an immunoaffinity purified anti-ERBB2 (phospho-Y1248) antibody (Upstate/Millipore Cat#06229). The Erbb2 phospho-Y1248 antibody was used to quantify tyrosine phosphorylation of Erbb2 resulting from the interaction of heregulin with Erbb3 and/or ErbB4. Hence, an increase in Y1248 phosphorylation of Erbb2 is expected when hESCs were incubated or pulsed with media in the presence of heregulin (lane 3; positive control), or pulsed with DC-HAIF media containing heregulin, Activin A, IGF1 and/or FGF (lane 5, "steady state"). Thus, lanes 3 and 5, where cultures were treated with media containing heregulin, show increased Erbb2 phosphorylation as detected by Erbb2 phospho-Y1248 antibody. The level of phospho-Y1248 was normalized with pan-phosphotyrosine control spots on RTK blots of the same samples. The steady-state sample was not normalized. Western blotting also demonstrated that AG825 inhibited autophosphorylation of ERBB2 at Tyrosine-1248 in hESC cultures incubated with media containing no growth factors (starved) and then later treated/pulsed with media containing heregulin and AG825 (FIG. 10, lanes 2 and 4). These results are consistent with the literature (Murillo H, Schmidt L J, Tindall D J. Cancer Res. 2001; 61:7408-7412). These findings demonstrated that disruption of ERBB2 signaling significantly inhibits hESC proliferation.

Example 15

The Tyrosine Kinase Inhibitor, AG825, Inhibits and Reduces the Proliferation and Cell Count of hESCs Based on the above studies described in Examples 13 and 14, further experiments were performed to quantify the number of hESCs and determine the level of inhibition of Erbb2 using AG825. Table 1 describes the cell count in these studies. These results demonstrated that there was a statistically significant decrease in the number of hESCs after treatment with AG825 as compared to the DMSO and conditioned media (CM) control. Values reported were taken from an average of the triplicate (3) cell counts. The initial cell count was performed similarly. AG825 inhibited Erbb2 tyrosine kinase activity, thereby inhibiting cell signaling, and effectively reducing and inhibiting HESC proliferation and growth by about at least 1, 2 or 3 orders of magnitude.

TABLE 1

AG825 inhibits Erbb2 and Erbb2 signaling thereby inhibiting hESCs proliferation.

| | Initial Cell Count No. | Conditioned Media (CM) | DMSO* | AG825* |
|---|---|---|---|---|
| Experiment 1 | $560 \times 10^3$ | $1.99 \times 10^6$ | $2.13 \times 10^6$ | $406.6 \times 10^3$ |
| Experiment 2 | $853.3 \times 10^3$ | $2.77 \times 10^6$ | $2.54 \times 10^6$ | $433.3 \times 10^3$ |

*P = 0.005 for Experiment 1; and P = 0.007 for Experiment 2.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

SEQUENCE LISTING

```
<160> NUMBER OF SEQ ID NOS: 5

<210> SEQ ID NO 1
<211> LENGTH: 1255
<212> TYPE: PRT
<213> ORGANISM: Homo sapiens

<400> SEQUENCE: 1

Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95
```

```
Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Thr Thr Pro
        115                 120                 125

Val Thr Gly Ala Ser Pro Gly Leu Arg Glu Leu Gln Leu Arg Ser
    130                 135                 140

Leu Thr Glu Ile Leu Lys Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
                195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510
```

-continued

```
Gln Leu Cys Ala Arg Gly His Cys Trp Gly Pro Gly Pro Thr Gln Cys
    515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
```

-continued

```
                    930                 935                 940
Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
                995                 1000                1005

Leu Glu Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Ala Pro Arg
                1060                1065                1070

Ser Pro Leu Ala Pro Ser Glu Gly Ala Gly Ser Asp Val Phe Asp Gly
                1075                1080                1085

Asp Leu Gly Met Gly Ala Ala Lys Gly Leu Gln Ser Leu Pro Thr His
                1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
                1140                1145                1150

Arg Glu Gly Pro Leu Pro Ala Ala Arg Pro Ala Gly Ala Thr Leu Glu
                1155                1160                1165

Arg Pro Lys Thr Leu Ser Pro Gly Lys Asn Gly Val Val Lys Asp Val
                1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
                1220                1225                1230

Pro Pro Ser Thr Phe Lys Gly Thr Pro Thr Ala Glu Asn Pro Glu Tyr
                1235                1240                1245

Leu Gly Leu Asp Val Pro Val
    1250                1255

<210> SEQ ID NO 2
<211> LENGTH: 4576
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2
ggaggaggtg gaggaggagg gctgcttgag gaagtataag aatgaagttg tgaagctgag     60
attcccctcc attgggaccg gagaaaccag gggagccccc cgggcagccg cgcgcccctt    120
cccacggggc cctttactgc gccgcgcgcc cggccccac ccctcgcagc accccgcgcc     180
```

-continued

| | |
|---|---|
| ccgcgccctc ccagccgggt ccagccggag ccatggggcc ggagccgcag tgagcaccat | 240 |
| ggagctggcg gccttgtgcc gctgggggct cctcctcgcc ctcttgcccc ccggagccgc | 300 |
| gagcacccaa gtgtgcaccg gcacagacat gaagctgcgg ctccctgcca gtcccgagac | 360 |
| ccacctggac atgctccgcc acctctacca gggctgccag gtggtgcagg gaaacctgga | 420 |
| actcacctac ctgcccacca atgccagcct gtccttcctg caggatatcc aggaggtgca | 480 |
| gggctacgtg ctcatcgctc acaaccaagt gaggcaggtc ccactgcaga ggctgcggat | 540 |
| tgtgcgaggc acccagctct ttgaggacaa ctatgccctg ccgtgctag acaatggaga | 600 |
| cccgctgaac aataccaccc ctgtcacagg ggcctcccca ggaggcctgc gggagctgca | 660 |
| gcttcgaagc ctcacagaga tcttgaaagg aggggtcttg atccagcgga accccagct | 720 |
| ctgctaccag gacacgattt tgtggaagga catcttccac aagaacaacc agctggctct | 780 |
| cacactgata gacaccaacc gctctcgggc ctgccacccc tgttctccga tgtgtaaggg | 840 |
| ctcccgctgc tggggagaga gttctgagga ttgtcagagc ctgacgcgca ctgtctgtgc | 900 |
| cggtggctgt gcccgctgca aggggccact gcccactgac tgctgccatg agcagtgtgc | 960 |
| tgccggctgc acgggcccca agcactctga ctgcctggcc tgcctccact caaccacag | 1020 |
| tggcatctgt gagctgcact gcccagccct ggtcacctac aacacagaca cgtttgagtc | 1080 |
| catgcccaat cccgagggcc ggtatacatt cggcgccagc tgtgtgactg cctgtccccta | 1140 |
| caactacctt tctacggacg tgggatcctg caccctcgtc tgccccctgc acaaccaaga | 1200 |
| ggtgacagca gaggatggaa cacagcggtg tgagaagtgc agcaagccct gtgcccgagt | 1260 |
| gtgctatggt ctgggcatgg agcacttgcg agaggtgagg gcagttacca gtgccaatat | 1320 |
| ccaggagttt gctggctgca agaagatctt tgggagcctg gcatttctgc cggagagctt | 1380 |
| tgatggggac ccagcctcca acactgcccc gctccagcca gagcagctcc aagtgtttga | 1440 |
| gactctggaa gagatcacag gttacctata catctcagca tggccggaca gcctgcctga | 1500 |
| cctcagcgtc ttccagaacc tgcaagtaat ccggggacga attctgcaca atggcgccta | 1560 |
| ctcgctgacc ctgcaagggc tgggcatcag ctggctgggg ctgcgctcac tgagggaact | 1620 |
| gggcagtgga ctggccctca tccaccataa caccccacctc tgcttcgtgc acacggtgcc | 1680 |
| ctgggaccag ctctttcgga acccgcacca agctctgctc cacactgcca accgccaga | 1740 |
| ggacgagtgt gtgggcgagg gcctggcctg ccaccagctg tgcgcccgag ggcactgctg | 1800 |
| gggtccaggg cccacccagt gtgtcaactg cagccagttc cttcggggcc aggagtgcgt | 1860 |
| ggaggaatgc cgagtactgc aggggctccc cagggagtat gtgaatgcca ggcactgttt | 1920 |
| gccgtgccac cctgagtgtc agccccagaa tggctcagtg acctgttttg gaccggaggc | 1980 |
| tgaccagtgt gtggcctgtg cccactataa ggaccctccc ttctgcgtgg cccgctgccc | 2040 |
| cagcggtgtg aaacctgacc tctcctacat gcccatctgg aagtttccag atgaggaggg | 2100 |
| cgcatgccag ccttgcccca tcaactgcac ccactcccct ctgacgtcca tcatctctgc | 2160 |
| ggtggttggc attctgctgg tcgtggtctt ggggtggtc tttgggatcc tcatcaagcg | 2220 |
| acggcagcag aagatccgga agtacacgat gcggagactc tgcaggaaa cggagctggt | 2280 |
| ggagccgctg acacctagcg gagcgatgcc caaccaggcg cagatgcgga tcctgaaaga | 2340 |
| gacggagctg aggaaggtga aggtgcttgg atctggcgct tttggcacag tctacaaggg | 2400 |
| catctggatc cctgatgggg agaatgtgaa aattccagtg gccatcaaag tgttgaggga | 2460 |
| aaacacatcc cccaaagcca acaaagaaat cttagacgaa gcatacgtga tggctggtgt | 2520 |
| gggctcccca tatgtctccc gccttctggg catctgcctg acatccacgg tgcagctggt | 2580 |

```
gacacagctt atgccctatg gctgcctctt agaccatgtc cgggaaaacc gcggacgcct    2640
gggctcccag gacctgctga actggtgtat gcagattgcc aaggggatga gctacctgga    2700
ggatgtgcgg ctcgtacaca gggacttggc cgctcggaac gtgctggtca agagtcccaa    2760
ccatgtcaaa attacagact tcgggctggc tcggctgctg acattgacg agacagagta     2820 ccatgcagat gggggcaagg tgcccatcaa gtggatggcg ctggagtcca ttctccgccg    2880
gcggttcacc caccagagtg atgtgtggag ttatggtgtg actgtgtggg agctgatgac    2940 ttttgggggcc aaaccttacg atgggatccc agcccgggag atccctgacc tgctggaaaa   3000
gggggagcgg ctgccccagc cccccatctg caccattgat gtctacatga tcatggtcaa    3060
atgttggatg attgactctg aatgtcggcc aagattccgg gagttggtgt ctgaattctc    3120
ccgcatggcc agggacccc agcgctttgt ggtcatccag aatgaggact gggcccagc      3180 cagtcccttg gacagcacct tctaccgctc actgctggag gacgatgaca tggggggacct   3240 ggtggatgct gaggagtatc tggtaccca gcagggcttc ttctgtccag accctgcccc     3300
gggcgctggg ggcatggtcc accacaggca ccgcagctca tctaccagga gtggcggtgg   3360
ggacctgaca ctagggctgg agccctctga agaggaggcc cccaggtctc cactggcacc    3420
ctccgaaggg gctggctccg atgtatttga tggtgacctg gaatgggggg cagccaaggg   3480
gctgcaaagc ctccccacac atgaccccag ccctctacag cggtacagtg aggacccac    3540 agtaccctg cctctgaga ctgatggcta cgttgcccc ctgacctgca gcccccagcc       3600
tgaatatgtg aaccagccag atgttcggcc ccagcccct tcgccccgag agggccctct    3660
gcctgctgcc cgacctgctg gtgccactct ggaaagggcc aagactctct ccccagggaa   3720
gaatggggtc gtcaaagacg tttttgcctt tgggggtgcc gtggagaacc ccgagtactt   3780
gacaccccag ggaggagctg cccctcagcc ccaccctcct cctgccttca gcccagcctt   3840
cgacaacctc tattactggg accaggaccc accagagcgg ggggctccac ccagcacctt   3900
caaagggaca cctacggcag agaacccaga gtacctgggt ctggacgtgc cagtgtgaac   3960
cagaaggcca agtccgcaga agccctgatg tgtcctcagg gagcagggaa ggcctgactt   4020
ctgctggcat caagaggtgg gagggccctc cgaccacttc caggggaacc tgccatgcca   4080
ggaacctgtc ctaaggaacc ttccttcctg cttgagttcc cagatggctg aaggggtcc    4140 agcctcgttg gaagaggaac agcactgggg agtctttgtg gattctgagg ccctgcccaa   4200
tgagactcta gggtccagtg gatgccacag cccagcttgg ccctttcctt ccagatcctg   4260
ggtactgaaa gccttaggga agctggcctg agagggaag cggccctaag ggagtgtcta    4320
agaacaaaag cgaccattc agagactgtc cctgaaacct agtactgccc cccatgagga   4380
aggaacagca atggtgtcag tatccaggct ttgtacagag tgcttttctg tttagttttt   4440 acttttttg ttttgtttt ttaaagatga aataaagacc caggggggaga atgggtgttg    4500 tatggggagg caagtgtggg gggtccttct ccacacccac tttgtccatt tgcaaatata   4560
ttttggaaaa cagcta                                                  4576
```

<210> SEQ ID NO 3
<211> LENGTH: 1239
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
             35                  40                  45

Leu Tyr Gln Gly Cys Gln Val Val Gln Gly Asn Leu Glu Leu Thr Tyr
         50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
         115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415
```

-continued

```
Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Pro Leu Thr Ser Ile Ile Ser
625                 630                 635                 640

Ala Val Val Gly Ile Leu Leu Val Val Val Leu Gly Val Val Phe Gly
                645                 650                 655

Ile Leu Ile Lys Arg Arg Gln Gln Lys Ile Arg Lys Tyr Thr Met Arg
            660                 665                 670

Arg Leu Leu Gln Glu Thr Glu Leu Val Glu Pro Leu Thr Pro Ser Gly
        675                 680                 685

Ala Met Pro Asn Gln Ala Gln Met Arg Ile Leu Lys Glu Thr Glu Leu
    690                 695                 700

Arg Lys Val Lys Val Leu Gly Ser Gly Ala Phe Gly Thr Val Tyr Lys
705                 710                 715                 720

Gly Ile Trp Ile Pro Asp Gly Glu Asn Val Lys Ile Pro Val Ala Ile
                725                 730                 735

Lys Val Leu Arg Glu Asn Thr Ser Pro Lys Ala Asn Lys Glu Ile Leu
            740                 745                 750

Asp Glu Ala Tyr Val Met Ala Gly Val Gly Ser Pro Tyr Val Ser Arg
        755                 760                 765

Leu Leu Gly Ile Cys Leu Thr Ser Thr Val Gln Leu Val Thr Gln Leu
    770                 775                 780

Met Pro Tyr Gly Cys Leu Leu Asp His Val Arg Glu Asn Arg Gly Arg
785                 790                 795                 800

Leu Gly Ser Gln Asp Leu Leu Asn Trp Cys Met Gln Ile Ala Lys Gly
                805                 810                 815

Met Ser Tyr Leu Glu Asp Val Arg Leu Val His Arg Asp Leu Ala Ala
            820                 825                 830

Arg Asn Val Leu Val Lys Ser Pro Asn His Val Lys Ile Thr Asp Phe
```

-continued

```
                835                 840                 845
Gly Leu Ala Arg Leu Leu Asp Ile Asp Glu Thr Glu Tyr His Ala Asp
850                 855                 860
Gly Gly Lys Val Pro Ile Lys Trp Met Ala Leu Glu Ser Ile Leu Arg
865                 870                 875                 880
Arg Arg Phe Thr His Gln Ser Asp Val Trp Ser Tyr Gly Val Thr Val
                885                 890                 895
Trp Glu Leu Met Thr Phe Gly Ala Lys Pro Tyr Asp Gly Ile Pro Ala
                900                 905                 910
Arg Glu Ile Pro Asp Leu Leu Glu Lys Gly Glu Arg Leu Pro Gln Pro
                915                 920                 925
Pro Ile Cys Thr Ile Asp Val Tyr Met Ile Met Val Lys Cys Trp Met
                930                 935                 940
Ile Asp Ser Glu Cys Arg Pro Arg Phe Arg Glu Leu Val Ser Glu Phe
945                 950                 955                 960
Ser Arg Met Ala Arg Asp Pro Gln Arg Phe Val Val Ile Gln Asn Glu
                965                 970                 975
Asp Leu Gly Pro Ala Ser Pro Leu Asp Ser Thr Phe Tyr Arg Ser Leu
                980                 985                 990
Leu Glu Asp Asp Asp Met Gly Asp Leu Val Asp Ala Glu Glu Tyr Leu
                995                 1000                1005
Val Pro Gln Gln Gly Phe Phe Cys Pro Asp Pro Ala Pro Gly Ala Gly
        1010                1015                1020
Gly Met Val His His Arg His Arg Ser Ser Ser Thr Arg Ser Gly Gly
1025                1030                1035                1040
Gly Asp Leu Thr Leu Gly Leu Glu Pro Ser Glu Glu Glu Ala Pro Arg
                1045                1050                1055
Ser Pro Leu Ala Pro Ser Glu Gly Ala Gly Ser Asp Val Phe Asp Gly
        1060                1065                1070
Asp Leu Gly Met Gly Ala Ala Lys Gly Leu Gln Ser Leu Pro Thr His
        1075                1080                1085
Asp Pro Ser Pro Leu Gln Arg Tyr Ser Glu Asp Pro Thr Val Pro Leu
        1090                1095                1100
Pro Ser Glu Thr Asp Gly Tyr Val Ala Pro Leu Thr Cys Ser Pro Gln
1105                1110                1115                1120
Pro Glu Tyr Val Asn Gln Pro Asp Val Arg Pro Gln Pro Pro Ser Pro
                1125                1130                1135
Arg Glu Gly Pro Leu Pro Ala Ala Arg Pro Ala Gly Ala Thr Leu Glu
        1140                1145                1150
Arg Ala Lys Thr Leu Ser Pro Gly Lys Asn Gly Val Val Lys Asp Val
        1155                1160                1165
Phe Ala Phe Gly Gly Ala Val Glu Asn Pro Glu Tyr Leu Thr Pro Gln
        1170                1175                1180
Gly Gly Ala Ala Pro Gln Pro His Pro Pro Pro Ala Phe Ser Pro Ala
1185                1190                1195                1200
Phe Asp Asn Leu Tyr Tyr Trp Asp Gln Asp Pro Pro Glu Arg Gly Ala
                1205                1210                1215
Pro Pro Ser Thr Phe Lys Gly Thr Pro Thr Ala Glu Asn Pro Glu Tyr
                1220                1225                1230
Leu Gly Leu Asp Val Pro Val
        1235

<210> SEQ ID NO 4
```

```
<211> LENGTH: 15
<212> TYPE: PRT
<213> ORGANISM: Homo sapiens

<400> SEQUENCE: 4

Ala Gly Ala Thr Leu Glu Arg Pro Lys Thr Leu Ser Pro Gly Lys
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Gly Ala Thr Leu Glu Arg Ala Lys Thr Leu Ser Pro Gly Lys
 1               5                  10                  15
```

We claim:

1. An isolated polypeptide comprising the amino acid sequence of SEQ ID NO:3 or a sequence having at least 99% amino acid sequence identity to full length SEQ ID NO:3, wherein said isolated polypeptide is an Erbb2 variant having a deletion of the amino acid sequence encoded by exon 16 of SEQ ID NO:1, and the amino acid residue at position 1155 of said SEQ ID NO:3 is not a proline residue.

2. The isolated polypeptide of claim 1, comprising the amino acid sequence of SEQ ID NO:3.

3. The isolated polypeptide of claim 1, wherein said Erbb2 variant has an alanine residue at amino acid position 1155 of SEQ ID NO:3.

4. The isolated polypeptide of claim 1, wherein said Erbb2 variant differs in its glycosylation profile from the wild type Erbb2 isoform encoded by SEQ ID NO:1.

* * * * *